(12) United States Patent
Xu et al.

(10) Patent No.: US 7,790,458 B2
(45) Date of Patent: Sep. 7, 2010

(54) MATERIAL AND METHODS FOR THE GROWTH OF HEMATOPOIETIC STEM CELLS

(75) Inventors: Ruiling Xu, Cary, NC (US); Andrea Liebmann-Vinson, Wake Forest, NC (US); Keith DeLuca, Fort Collins, CO (US); Mohammad Heidaran, Chatham, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 789 days.

(21) Appl. No.: 11/128,950

(22) Filed: May 13, 2005

(65) Prior Publication Data

US 2005/0272152 A1    Dec. 8, 2005

Related U.S. Application Data

(60) Provisional application No. 60/571,212, filed on May 14, 2004.

(51) Int. Cl.
  *C12N 5/02* (2006.01)
  *C12N 5/00* (2006.01)
  *C12N 5/071* (2006.01)
(52) U.S. Cl. .................. 435/406; 435/372; 435/384; 435/386; 435/387
(58) Field of Classification Search ................ 435/325, 435/372, 404, 386, 405, 406, 384
  See application file for complete search history.

(56) References Cited

U.S. PATENT DOCUMENTS

| | | | |
|---|---|---|---|
| 4,965,204 A | 10/1990 | Civin | |
| 5,035,994 A | 7/1991 | Civin | |
| 5,061,620 A | 10/1991 | Tsukamoto et al. | |
| 5,081,030 A | 1/1992 | Civin | |
| 5,130,144 A | 7/1992 | Civin | |
| 5,472,867 A | 12/1995 | Kanz et al. | |
| 5,541,103 A | 7/1996 | Kanz et al. | |
| 5,612,211 A | 3/1997 | Wilson et al. | |
| 5,635,387 A | 6/1997 | Fei et al. | |
| 5,643,741 A | 7/1997 | Tsukamoto et al. | |
| 5,665,557 A | 9/1997 | Murray et al. | |
| 5,677,136 A | 10/1997 | Simmons et al. | |
| 5,681,559 A | 10/1997 | DiGiusto et al. | |
| 5,695,755 A | 12/1997 | Papayannopoulou | |
| 5,716,827 A | 2/1998 | Tsukamoto et al. | |
| 5,728,581 A | 3/1998 | Schwartz et al. | |
| 5,750,397 A | 5/1998 | Tsukamoto et al. | |
| 5,807,686 A | 9/1998 | Wagner et al. | |
| 5,814,440 A | 9/1998 | Hill et al. | |
| 5,817,773 A | 10/1998 | Wilson et al. | |
| 5,827,742 A | 10/1998 | Scadden | |
| 5,876,956 A | 3/1999 | Colvin et al. | |
| 5,877,299 A | 3/1999 | Thomas et al. | |
| 5,905,041 A | 5/1999 | von Lindern et al. | |
| 5,914,108 A | 6/1999 | Tsukamoto et al. | |
| 5,925,567 A | 7/1999 | Kraus et al. | |
| 5,945,337 A | 8/1999 | Brown | |
| 5,972,627 A | 10/1999 | Galy | |
| 5,980,887 A | 11/1999 | Isner et al. | |
| 6,015,554 A | 1/2000 | Galy | |
| 6,030,836 A | 2/2000 | Thiede et al. | |
| 6,037,174 A | 3/2000 | Smith et al. | |
| 6,060,052 A | 5/2000 | Murray et al. | |
| 6,224,860 B1 | 5/2001 | Brown | |
| 6,225,119 B1 | 5/2001 | Qasba et al. | |
| 6,280,718 B1 | 8/2001 | Kaufman et al. | |
| 6,306,575 B1 | 10/2001 | Thomas et al. | |
| 6,335,195 B1 * | 1/2002 | Rodgers et al. | ............. 435/377 |
| 6,372,210 B2 | 4/2002 | Brown | |
| 6,429,012 B1 | 8/2002 | Kraus et al. | |
| 6,465,247 B1 | 10/2002 | Weissman et al. | |
| 6,537,807 B1 | 3/2003 | Smith et al. | |
| 6,586,192 B1 | 7/2003 | Peschle et al. | |
| 6,605,275 B1 | 8/2003 | Boyse et al. | |
| 6,613,568 B2 | 9/2003 | Kaufman et al. | |
| 6,667,034 B2 | 12/2003 | Palsson et al. | |
| 6,676,937 B1 | 1/2004 | Isner et al. | |
| 6,733,746 B2 * | 5/2004 | Daley et al. | ............. 424/93.21 |
| 6,761,883 B2 | 7/2004 | Weissman et al. | |
| 6,767,737 B1 | 7/2004 | Wilson et al. | |
| 6,852,533 B1 | 2/2005 | Rafii et al. | |
| 6,875,607 B1 | 4/2005 | Reubinoff et al. | |
| 6,875,608 B1 | 4/2005 | Smith et al. | |
| 2001/0031255 A1 | 10/2001 | Hoffman et al. | |
| 2001/0049139 A1 | 12/2001 | Lagasse et al. | |
| 2002/0022216 A1 | 2/2002 | Kraus et al. | |
| 2002/0031757 A1 | 3/2002 | Ohgushi et al. | |
| 2002/0037278 A1 | 3/2002 | Ueno et al. | |
| 2002/0051762 A1 | 5/2002 | Rafii et al. | |
| 2002/0061587 A1 | 5/2002 | Anversa | |
| 2002/0114789 A1 | 8/2002 | Peled et al. | |
| 2002/0132343 A1 | 9/2002 | Lum | |
| 2002/0142457 A1 | 10/2002 | Umezawa et al. | |

(Continued)

FOREIGN PATENT DOCUMENTS

WO    WO/03/022988    *    3/2003

(Continued)

OTHER PUBLICATIONS

Gupta et al Blood. 2000; 95(1): 147-55.*

(Continued)

*Primary Examiner*—Deborah Crouch
*Assistant Examiner*—Anoop Singh
(74) *Attorney, Agent, or Firm*—Alston & Bird, LLP

(57) ABSTRACT

The invention provides populations of expanded CD34-expressing cells and methods of use. Particular embodiments provide for defined culture media useful for growing these cells, and grafts comprising these cells. The invention finds use in methods for reconstituting, repairing, and regenerating tissue damage.

4 Claims, 3 Drawing Sheets

U.S. PATENT DOCUMENTS

| | | |
|---|---|---|
| 2002/0142462 A1 | 10/2002 | Ildstad et al. |
| 2002/0150561 A1 | 10/2002 | Kraus et al. |
| 2002/0159981 A1 | 10/2002 | Peled et al. |
| 2002/0159984 A1 | 10/2002 | Brown |
| 2002/0160512 A1 | 10/2002 | Shih |
| 2002/0164794 A1 | 11/2002 | Wernet |
| 2002/0197717 A1 | 12/2002 | Torok-Storn et al. |
| 2003/0003084 A1 | 1/2003 | Seshi |
| 2003/0008393 A1 | 1/2003 | Crooks et al. |
| 2003/0031651 A1 | 2/2003 | Lee et al. |
| 2003/0032185 A1 | 2/2003 | Sharkis et al. |
| 2003/0044978 A1 | 3/2003 | Murray et al. |
| 2003/0059414 A1 | 3/2003 | Ho et al. |
| 2003/0077824 A1 | 4/2003 | Rossi |
| 2003/0082805 A1 | 5/2003 | Murray et al. |
| 2003/0091547 A1 | 5/2003 | Edelberg et al. |
| 2003/0113303 A1 | 6/2003 | Schwartz |
| 2003/0124091 A1 | 7/2003 | Tuse et al. |
| 2004/0077985 A1 | 4/2004 | Rudd |
| 2004/0110286 A1 | 6/2004 | Bhatia |
| 2004/0121457 A1 | 6/2004 | Castellon |
| 2004/0121461 A1 | 6/2004 | Honmou et al. |
| 2004/0121464 A1 | 6/2004 | Rathjen et al. |
| 2004/0126879 A1 | 7/2004 | Schneider et al. |
| 2004/0131585 A1 | 7/2004 | Itescu |
| 2004/0132186 A1 | 7/2004 | Weissman et al. |
| 2004/0136966 A1 | 7/2004 | Anversa et al. |
| 2004/0136973 A1 | 7/2004 | Huberman et al. |
| 2004/0151700 A1 | 8/2004 | Chute et al. |
| 2004/0161419 A1 | 8/2004 | Strom et al. |
| 2004/0171147 A1 | 9/2004 | Hariri |
| 2004/0180432 A1 | 9/2004 | Emerson et al. |
| 2004/0197310 A1 | 10/2004 | Sanberg et al. |
| 2004/0203142 A1 | 10/2004 | Rai |
| 2004/0209357 A1 | 10/2004 | Xia et al. |
| 2004/0215334 A1 | 10/2004 | Fernandes et al. |
| 2004/0219136 A1 | 11/2004 | Hariri |
| 2004/0224403 A1 | 11/2004 | Bhatia |
| 2004/0228847 A1 | 11/2004 | Goldschmmidt-Clermont et al. |
| 2004/0235160 A1 | 11/2004 | Nishikawa et al. |
| 2004/0247575 A1 | 12/2004 | Caplice et al. |
| 2004/0248295 A1 | 12/2004 | Nawa et al. |
| 2004/0248796 A1 | 12/2004 | Alitalo et al. |
| 2004/0258670 A1 | 12/2004 | Laughlin et al. |
| 2005/0002933 A1 | 1/2005 | Baron et al. |
| 2005/0008624 A1 | 1/2005 | Peled et al. |
| 2005/0026220 A1* | 2/2005 | Rafii et al. .................. 435/7.2 |
| 2005/0032122 A1 | 2/2005 | Hwang et al. |
| 2005/0032218 A1 | 2/2005 | Gerlach |
| 2005/0037488 A1 | 2/2005 | Mitalipova et al. |
| 2005/0054097 A1* | 3/2005 | Peled et al. ................. 435/372 |
| 2005/0059083 A1 | 3/2005 | Liebmann-Vinson et al. |
| 2005/0276793 A1* | 12/2005 | Milhem et al. ............. 424/93.7 |
| 2006/0051330 A1* | 3/2006 | Hossfeld et al. .......... 424/93.21 |
| 2006/0281174 A1* | 12/2006 | Xu et al. .................... 435/325 |

FOREIGN PATENT DOCUMENTS

| | | | |
|---|---|---|---|
| WO | WO 03/046161 | * | 6/2003 |

OTHER PUBLICATIONS

Murray et al Exp Hematol. 1999; 27(6): 1019-28.*
Conley et al Int J Biochem Cell Biol. 2004, 36(4): 555-67.*
Odorico et al Stem Cells, vol. 19, No. 3, 193-204, 2001.*
Hofmeister et al Bone Marrow Transplantation (2007) 39, 11-23.*
Cabral, J. (Biotechnology Letters, 2001, 23, 741-751.*
Audent Biotechnology and bioengineering, 2002, 393-404, abstract.*
Zandstra et al PNAS, 1997, 4698-4703.*
Petzer et al Journal of Experimental Medicine, 1996, 183, 2551-2558.*
Long et al J. Clin. Invest. 1992. 90:251-255.*
Lataillade et al Blood, 2000; 95(3):756-68.*
Hiraoka et al Hematology Journal, 2001, 2(5): 307-315, abstract.*
Kawada et al, Rapid ex vivo expansion of human umbilical cord hematopoietic progenitors using a novel culture system, Experimental Hematology, vol. 27, No. 5, 1999, pp. 904-915.
Terstappen et al. Sequential generations of hematopoietic colonies derived from single nonlineage-committed CD34 positive CD38 . . . , Blood, vol. 77, No. 6, 1991, pp. 1218-1227.
Gratama et al., Flow cytometric enumeration of CD34+ hematopoietic stem and progenitor cells, Cytometry, vol. 34, No. 3, Jun. 15, 1998, pp. 128-142.
Piacibello et al., Engraftment in non-obese diabetic severe combined immunodeficient mice of human CD34+. . . , Blood, vol. 93, Jun. 1, 1999, pp. 3736-3749.
Xu et al., Serum supplement, inoculum cell density, and accessory cell effects are dependent on the cytokine combination . . . , Transfusion, vol. 40, No. 11, 2000, pp. 1299-1307.
Flores-Guzman et al., In vitro proliferation, expansion, and differentiation of a CD34+ cell-enriched hematopoietic . . . , Arch. of Med. Res., vol. 33, No. 2, 2002, pp. 107-114.
Lam et al., Preclinical ex vivo expansion of cord blood haematopoietic stem and progenitor cells . . . , Transfusion, vol. 41 (12), 2001, pp. 1567-1576.
Losordo, D.W., et al., "Therapeutic Angiogenesis and Vasculogensis for Ischemic Disease, Part II: Cell-Based Therapies," *Circulation*, Jun. 8, 2004, pp. 2692-2697.
Urbich, C., et al., "Endothelial Progenitor Cells, Characterization and Role in Vascular Biology," *Circulation Research*, Aug. 20, 2004, pp. 343-353.
Flores-Guzman, Patricia et al., "In Vitro Proliferation, Expansion, and Differentiation of a CD34+ Cell-Enriched Hematopoietic Cell Population from Human Umbilical Cord Blood in Response to Recombinant Cytokines," *Archives of Medical Research*, Mar.-Apr. 1001, pp. 107-114, vol. 33, No. 2.
Lam, Audrey C. et al., "Preclinical Ex Vivo Expansion of Cord Blood Hematopoietic Stem and Progenitor Cells: Duration of Culture; the Media, Serum Supplements, and Growth Factors Used; and Engraftment in NOD/SCID Mice," *Transfusion*, Dec. 2001, pp. 1567-1576, vol. 41, No. 12.
Piacibello, Wanda, et al., "Engraftment in Nonobese Diabetic Severe Combined Immunodeficient Mice of Human CD34+ Cord Blood Cells After Ex Vivo Expansion: Evidence for the Amplification and Self-Renewal of Repopulating Stem Cells," *Blood*, Jun. 1, 1999, pp. 3736-3749, vol. 93, No. 11.
Xu, Ruiling et al., "Serum Supplement, Inoculum Cell Density, and Accessory Cell Effects Are Dependent on the Cytokine Combination Selected to Expand Human HPCs Ex Vivo," *Transfusion*, Nov. 2000, pp. 1299-1307, vol. 40, No. 11.

* cited by examiner

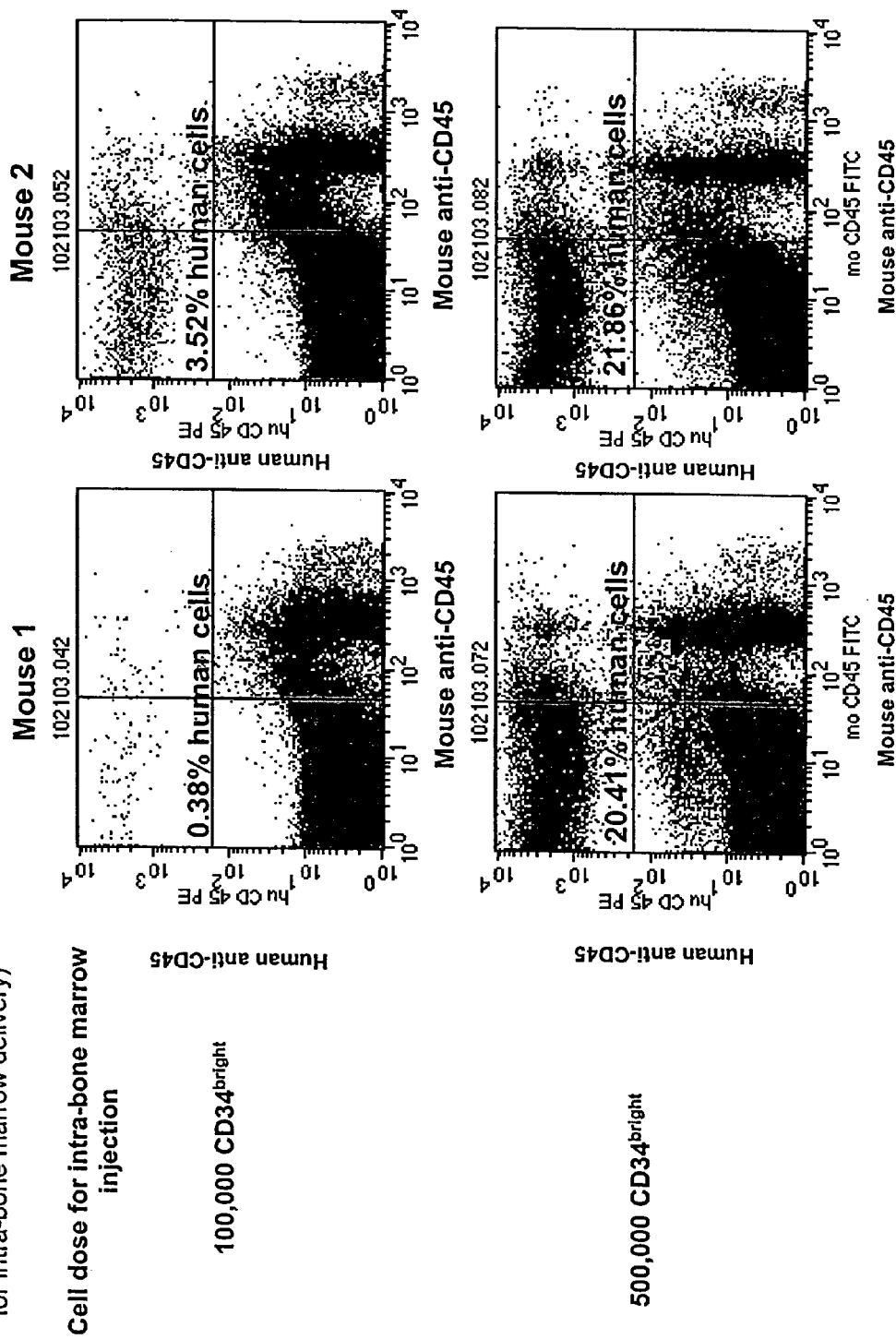

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: peptide sequence that can be present in
      hematopoietic adhesion protein

<400> SEQUENCE: 1

Val Thr Cys Gly
1
```

MATERIAL AND METHODS FOR THE GROWTH OF HEMATOPOIETIC STEM CELLS

CROSS-REFERENCE TO RELATED APPLICATIONS

This application claims the benefit of U.S. Provisional Application No. 60/571,212, filed May 14, 2004, the content of which is herein incorporated by reference in its entirety.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 291010SEQLIST.TXT, created on Feb. 23, 2010, and having a size of 581 bytes and is filed with the Response filed on Mar. 1, 2010. The sequence listing contained in this ASCII formatted document is part of the specification and is herein incorporated by reference in its entirety.

FIELD OF THE INVENTION

The present invention relates to stem cell populations and methods of expanding these stem cell populations. The invention also relates to methods of using the expanded stem cell populations.

BACKGROUND OF THE INVENTION

Throughout a lifetime, a small population of self-renewing stem cells continuously replenishes cells and tissues of the body. Stem cell sources such as bone marrow (BM), mobilized peripheral blood (MPB), fetal liver, placenta, embryonic stem cells, and umbilical cord blood (UCB) all contain a variety of stem and progenitor cells (SPC) capable of reconstituting various cell lineages. These SPC remain quiescent until specific biological signals induce differentiation and proliferation. However, the specific signals are rarely known.

Hematopoiesis is the process of blood cell development from stem cells residing in the adult bone marrow (Bonner, et al., "The Blood and the Lymphoid Organs," in *Pathology* (Rubin et al., eds., 1999), pp. 1051-1061). Hematopoietic stem cells (HSCs) in an adult typically reside in the bone marrow and the connective tissue filling up the cavities inside the long bones (breast bone, skull, hips, pelvic, ribs, and spine) of the body (Dexter and Spooncer (1987) *Annu. Rev. Cell. Biol.* 3:423; Verfaillie et al. (1999) 4:321), but have also been found in umbilical cord blood (UCB), mobilized peripheral blood, and placenta, and they have been derived from embryonic stem cells. The connective tissue consists of a complex network of solid cords separated by sinusoids. The cords are composed of stromal and hematopoietic cells, knitted together by an extensive and fertile extracellular matrice (ECM) (Bonner, et al., "The Blood and the Lymphoid Organs," in *Pathology* (Rubin et al., eds., 1999), pp. 1051-1061). Arteries and capillaries within the bone provide blood and nutrients to the cells of the bone marrow.

Hematopoietic stem cells can be divided into four categories based on their ability to self-renew and commitment to a certain cell lineage: (i) pluripotential stem cells with unlimited self-renewal capacity; (ii) multipotential progenitor cells, also with unlimited self-renewing capacity, but committed to either lymphoid or non-lymphoid cell lineages; (iii) unipotential progenitor cells with limited self-renewal capacity and commitment to discrete blood cell lineages; and (iv) differentiated precursor cells with no self-renewing ability (Bonner, et al., "The Blood and the Lymphoid Organs," in *Pathology* (Rubin et al., eds., 1999), pp. 1051-1061; and Cabrita et al. (2003) *Trends Biotechnol.* 21:233.)

Hematopoietic stem cells are commonly classified by the presence or absence of cell surface antigens (surface markers). CD34, which is the most commonly accepted marker for hematopoietic stem cells, is believed to be expressed on HSCs as well as on the majority of committed progenitors. See, for example, Yu et al. (1996) *J. Formos. Med. Assoc.* 95:281. Selection of CD34$^+$ cells from bone marrow, peripheral blood, or cord blood will thus lead to a heterogeneous cell mixture containing not only primitive HSCs but also more mature, lineage specific progenitors. Id. CD34 expression on human hematopoietic stem cells is reversible. See, for example, Nolta et al. (2002) *Leukemia* 16(3):352-61. Human CD34$^+$CD38$^-$ cells after long-term engraftment (7-18 months) in bnx mice lost expression of CD34 as they became deeply quiescent. Id. A CD45$^+$CD34$^-$Lineage$^-$ cell population recovered from the bone marrow of mice after long-term engraftment of CD34$^+$CD38$^-$ cells was able to create colony-forming units contained long-term culture initiating cells (LTC-IC) and gave rise to multilineage engraftment with up-regulation of CD34 expression in secondary, immune-deficient mice. Id. CD34$^+$CD38$^-$ cells are believed to be one of the most primitive populations of stem/progenitor cells that have been identified to date. See, for example, Nolta et al. (2002) *Leukemia* 16(3):352-61. Lack of, or very low level, expression of HLA-DR (human leukocyte antigen-locus DR) has been associated with extensive in vitro expansion capacity and in vivo stem cell function. See, for example, Yu et al. (1996) *J. Formos. Med. Assoc.* 95:281. An increase in HLA-DR expression on adult bone marrow or peripheral blood derived cells was found to correlate with lineage commitment. Id. In contrast, fetal as well as cord blood HSCs were reported to express HLA-DR. Id. Thy-1 expressed at low levels characterizes a subset of CD34$^+$ cells with stem cell function. Id. CD133, also sometimes called AC133, is another cell surface marker commonly associated with hematopoietic stem cells.

Some researchers have attempted to expand stem cells ex vivo using defined cytokine cocktails with and without animal-derived serum and with and without cell feeder layers. See, for example, Dexter and Spooncer (1987) *Annu. Rev. Cell. Biol.* 3:423; Verfaillie et al. (1999) 4:321; Donovan and Gearhart (2001) *Nature* 414:92; Dexter et al. (1984) *Blood Cells* 10:315. It is widely accepted that using stroma-free, cytokine-supplemented cultures results in a large mature cell expansion. In fact, in most cases it is observed that the number of long-term culture initiating cells (LTC-IC) steadily decline indicating that expanded stem cells lose their developmental potential in culture, and that this potential eventually drops below the input level. See, for example, Yu et al. (1996) *J. Formos. Med. Assoc.* 95:281. Systems requiring animal-derived serum or exogenous feeder cells increase the risk of adverse immunogenicity reactions and the occurrence of infection in the recipient. Thus, there is a need in the art for chemically well-defined, such as cytokine-supplemented, cultures that sustain HSC growth over time, such that the amount of cells does not drop below the input level.

If stem cells capable of reconstituting particular lineages can be in vitro expanded and the developmental potential maintained, then therapies can be improved by decreasing the amount of donor material needed for therapy. Expanded SPC have the potential for use in stem cell transplantation in cancer therapy. In addition, the potential use of SPCs in other cellular therapies has been demonstrated, such as diabetes, heart disease, liver regeneration, and neurodegenerative diseases.

Another potential area of application for expanded SPCs is tissue engineering. A common problem encountered in tissue engineering applications, where culture-expanded cells can be used to create custom grafts of any size or shape to reconstitute, repair, and replace damaged or diseased tissues, is providing sufficient nutrients to cells residing inside solid engineered tissues exceeding a certain size. Certain SPCs, such as endothelial progenitor cells, have recently been shown to initiate neovascularization.

Neovascularization (formation of new blood vessels) can result from one of two distinct processes, vasculogenesis or angiogenesis. Vasculogenesis involves differentiation of endothelial progenitor cells (EPCs) into endothelial cells during embryogenesis. Angiogenesis entails the sprouting of capillaries from existing blood vessels. Commonly used strategies to induce neovascularization are focused on using controlled release of growth factors or DNA to promote angiogenesis, and only a few studies have attempted to utilize endothelial progenitor cells in combination with growth factor delivery. Importantly, stem cell culture systems would obviate the practical limitations associated with fresh donor material because stem cells can be frozen and then expanded prior to use. Thus, methods for the expansion of SPC are needed.

Megakaryocytes reside in the bone marrow and are the precursors to platelets. As compared to bone marrow (BM) and mobilized peripheral blood stem cell (mPBSC) transplants, engraftment to platelets is significantly delayed in cord blood stem cell transplants, i.e., 9 days for mPBSC as compared to anywhere from 56 to over 200 days. During this time, a patient is susceptible to bleeding and receives platelet transfusions to mitigate this problem. There is thus a need to shorten the time to platelet engraftment for patients receiving cord blood stem cell transplants to reduce the risk of bleeding, the need for platelet transfusions over an extended period of time, and ultimately to reduce the time of the hospital stay following the transplant.

SUMMARY OF THE INVENTION

The present invention provides compositions and methods for promoting hematopoietic stem and progenitor cell expansion. In preferred embodiments, the expansion of these cells results from the use of one of six different media compositions (cytokine cocktails): G2, F2, D6, F2N, F4, or G8. When cells are expanded using these cocktails, a large portion of the cells maintain CD34 expression. The invention further relates to an expanded hematopoietic stem and progenitor cell population characterized by a high level of CD34 expression. The cells containing a high level of CD34 expression are referred to as $CD34^{br}$ cells. By expanding hematopoietic stem and progenitor cells in medium G2, F2, D6, F2N, F4, or G8, the number of cells expressing CD34 at high level, e.g., $CD34^{br}$, is increased significantly. This finding is significant, because the level of CD34 expression typically diminishes as a consequence of in vitro expansion of hematopoietic stem and progenitor cells. As CD34 is expressed on HSCs and the majority of committed progenitors, a cell population resulting from in vitro culture that contains a high number of $CD34^+$ cells is desirable because the population represents a variety of cells and therefore is ideal for cellular therapy. Furthermore, the $CD34^{br}$ cells of the invention maintain a high plating efficiency, similar to freshly isolated $CD34^+$ cells. This supports the conclusion that the $CD34^{br}$ population contains a number of stem and progenitor cells, comparable to freshly isolated $CD34^+$ cells. In addition, in colony forming assays, $CD34^{br}$ cells lead to a high number of mixed colonies, further indicating the presence of multipotential stem and progenitor cells. When the expanded cells are transplanted, many cells types can be reconstituted including megakaryocytes and neutrophils.

In a preferred embodiment of the invention, the starting population of the cell culture is obtained from umbilical cord blood (UBC) cells by eliminating the majority of mature cells and thus enriching for the more immature $CD34^+$ cells. Purities are commonly better than 75%. Other sources of $CD34^+$ cells may be used, such as bone marrow and peripheral blood cells or fetal liver. Alternatively, CD133+ cells from these sources may also be used.

The invention also encompasses methods for expanding and enriching $CD34^+$ HSC and progenitor cells. The cells may be enriched via direct and or indirect isolation methods that are known in the art. The purity of the cells may then be determined by methods know in the art, such as flow cytometry. Enriched cells are then seeded and cultured in a media that supports cell expansion. Optionally a growth factor may be added, such as vascular endothelial growth factor (VEGF). Alternatively, the HSC and progenitor cells may be expanded in culture first, and then enriched for $CD34^+$ or $CD34^{br}$ via isolation and purification methods. Alternatively, CD133+ cells from these sources may also be used.

Various culture methods may be employed in the methods of the present invention including the use of sheets, slides, dishes (e.g., petri dishes), culture flasks, bags, and multiwell cluster dishes of any number and geometric layout of wells. In a preferred embodiment of the invention, three-dimensional structures (3-D; also commonly called scaffolds) are used in culturing these cells. The cells can be either freshly isolated; expanded; expanded and differentiated into endothelial progenitor cells (EPCs) or endothelial cells; or presorted based on phenotype, such as $CD34^+$, $CD34^+/CD133^+$, $CD34^+/CD31^+$, etc. Cells may be expanded or differentiated with or without the use of the growth factors such as VEGF or bFGF. Scaffolds are of particular interest in this invention due to their compatibility in cellular therapies, as 3-D scaffolds more closely mimic living tissues.

The invention also relates to compositions for the creation of vascular tissue comprising expanded cells and any scaffold material such as alginates or hyaluronic acid, microsphere-based approaches, or fiber-based mesh approaches, coupled with a therapeutic cell such as islets, insulin-producing cells, hepatocytes, bone, kidney, heart, and the like.

In a further aspect of the invention, this composition may be used in methods of producing cell/scaffold constructs with therapeutic, angiogenic, or vasculogenic cells, methods of culturing these constructs, and transplantation.

Another aspect of the invention speaks to the methods and use of the enriched, expanded cell population for a variety of cellular therapies such as reconstitution of the hematopoietic system following high dose radiation or chemotherapy, reconstitution of megakaryocytes (and thereby platelets) after myelo-ablative therapies, induction of vascularization of scaffolds in vivo, and application of the cells in ischemic cardiomyopathies, and in the treatment of diabetes.

In one embodiment, expanded stem cell populations and methods for their use are provided. The expanded stem cell populations maintain clonogenic potential indicating that the cell populations comprise immature and mature progenitor cells and multipotential hematopoietic stem cells. Thus, the methods of the invention find use in producing long-term repopulating cells, in culture, without the loss of developmental potential of the cells. The expanded cell populations are useful for therapeutic applications in the treatment of cancer, diabetes, heart disease, neurodegenerative disease, liver regeneration, and tissue engineering. In particular, the expanded populations can be used for ameliorating diseases such as cancer and anemia, and in situations where it is desirable to obtain more committed cell types such as ischemic cardiomyopathies, and diabetes. The cell populations can be used to improve or to promote vascularization, including promoting vascularization of tissue implants or ischemic heart tissue. Likewise, the cells can be used to regenerate or repair damaged organs or tissues. The expanded cell populations can be genetically modified to express exogenous genes of interest. The genetically modified cells can be used to produce stably transformed, transfected, or transduced stem cells that express a gene of interest, e.g., a therapeutic agent. Such cells are useful in treatment of diseases, in particular genetic diseases in the patient.

In one aspect, the invention provides growth factor combinations and culture media suitable for hematopoietic stem and progenitor cell expansion. In a preferred embodiment, the growth factor combinations and culture media are effective for the expansion of cord blood-derived $CD34^+$, $CD133^+$, or $Lin^-$ cells, and use thereof results in a population of $CD34^+$ cells that is characterized by a high level of CD34 expression. Bone marrow and peripheral blood cells may also be used. Six media compositions (cytokine cocktails) designated G2, F2, D6, F2N, F4, and G8 are disclosed. All of the cytokine cocktails are capable of either supporting or maintaining, or both supporting and maintaining, the proliferation of $CD34^+$ cells when added to nutritive media. In fact, the cocktails are capable of expanding hematopoietic stem cells, and mature and immature progenitor cells.

BRIEF DESCRIPTION OF THE DRAWINGS

FIG. 3 shows the engraftment level of expanded human cells into mouse bone marrow at various inoculation doses.

DETAILED DESCRIPTION OF THE INVENTION

Figure 1:
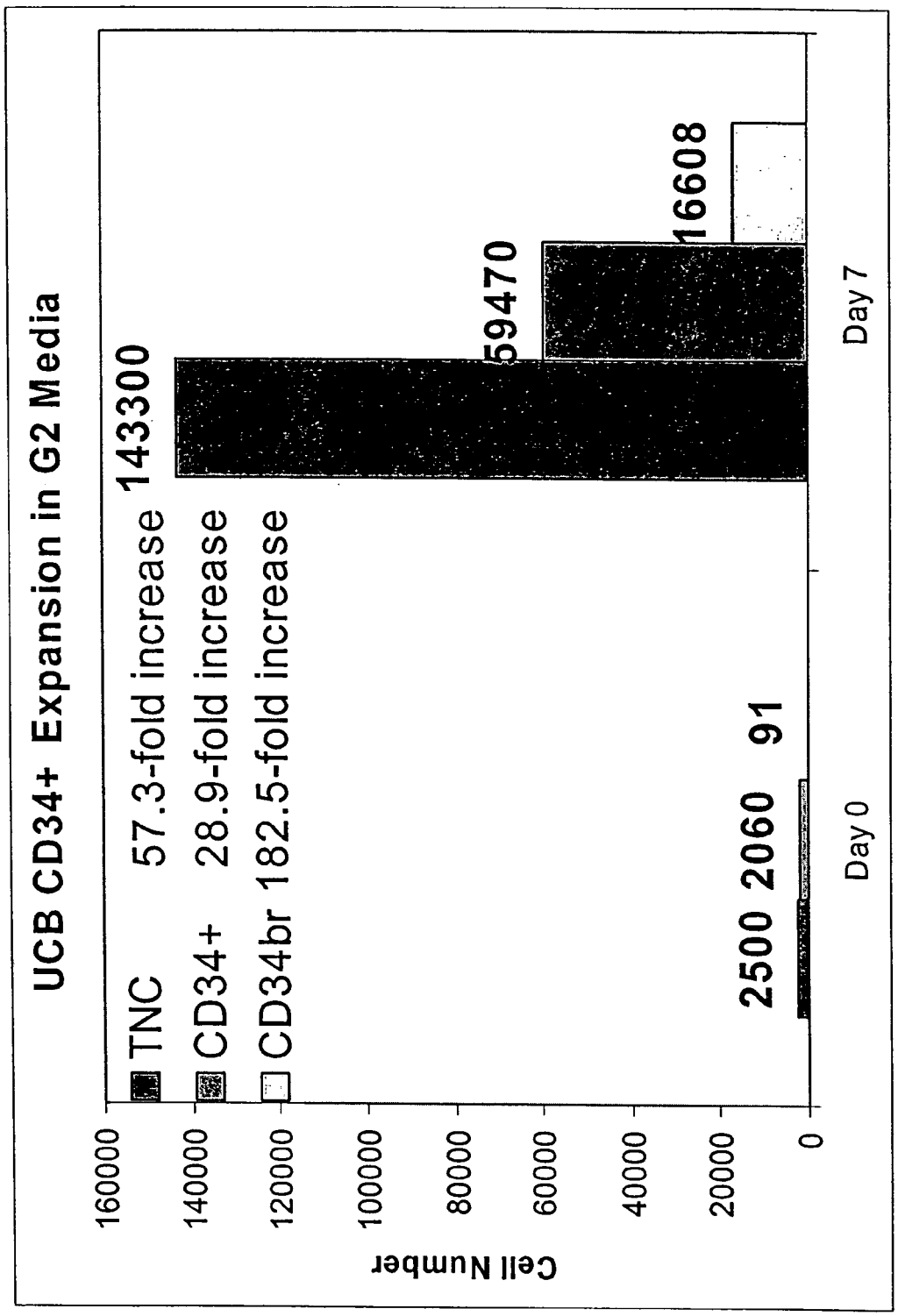
FIG. 1 shows the relative increases of total nucleated cells, the $CD34^+$ cell population, and $CD34^{br}$ cell population after culture in G2 medium.

Expanded stem cell populations and methods for their use are provided. The stem cells are expanded in distinct media compositions comprising a mixture of cytokines. The expanded stem cell populations are characterized by the ability to give rise to various hematopoietic and mesenchymal cell types that can reconstitute, repair, and regenerate damaged organs by grafting these cells into patients in need thereof. The term "expanded" is intended to mean that the resultant cell population is derived from ex vivo culture of stem cells in media compositions comprising mixtures of cytokines, where the outgoing (cultured) number of cells exceeds the ingoing (non-cultured) number of cells. The term "expanded" is not to be construed or limited by any mechanism or theory of cellular origin and may comprise cells that originate de novo in culture, cells that simply increase in expression of the CD34 antigen, or combinations thereof.

In some embodiments, the expanded stem cell populations are characterized as comprising a mix of cell types, including but not limited to BFU-E/CFU-E (burst-forming unit-erythroid/colony forming unit erythroid, e.g., colonies characteristic for erythroid progenitor cells), CFU-GM (colony forming units-granulocyte/macrophage, e.g., neutrophil/monocyte progenitors), CFU-G (neutrophil progenitors), CFU-GEMM (colony-forming unit-granulocyte, -erythrocyte, -monocyte, and -megakaryocyte, e.g., characteristic for more immature myeloid stem cells), mesenchymal progenitors such as endothelial progenitor cells, and combinations thereof. In yet other embodiments, the expanded stem cell population is substantially free of T-cells (CD3), B-cells (CD19), or mature granulocytes, NK lymphocytes, or macrophages (CD16).

The term "substantially free" is intended to mean that less than 5%, less than 4%, less than 3%, less than 2%, or less than 1% of the cells within the population express the marker of interest. A small number of monocytes (CD14) and platelets or megakaryocytes (CD42a) may be present in the population. A substantial proportion of cells may express surface markers characteristic of endothelial cells, platelets, leukocytes or their precursors (CD31), of myeloid progenitor cells (CD33), of hematopoietic stem and progenitor cells (CD34), of proliferating cells and erythroid precursors (CD71), and of $CD34^{br}$ stem and progenitor cells or neural or hematopoietic stem cells (CD133). The term "substantial proportion" is intended to mean that at least 40%, at least 50%, at least 60%, at least 70%, at least 80%, at least 90%, at least 95%, at least 99%, up to 100% of the cells express the marker of interest. The expression of CD38, a marker typically expressed on differentiating hematopoietic cells, is substantially diminished after culture. The term "substantially diminished" is intended to mean that at least less than 10%, less than 5% of the cells express the marker of interest.

These expanded cells are also characterized by a capacity for self-renewal and are therefore clonogenic. "Clonogenic" is intended to mean that the progeny of a single cell can be identified. Further, the cells are characterized by an ability to commit to multilineage development. By "multilineage development" is intended that the cell is capable of differentiating into cell types of hematopoietic or endothelial origin. Self renewing multilineage stem cells are capable of long-term engraftment. By "long-term engraftment" is intended that when grafted into a host, the stem cells remain engrafted for greater than 6 weeks. See, for example, Osawa et al. (1996) *Science* 273:242; Goodell et al. (1996) *J. Exp. Med.* 183:1797, Prosper et al. (2001) *J. Leukoc. Biol.* 69:307-16; Yu (1996) *J. Formos Med. Assoc.* 95:281-93; Bonner, et al., "The Blood and the Lymphoid Organs," in *Pathology* (Rubin et al., eds., 1999), pp. 1051-1061. Conversely, short-term engrafting stem cells are termed "progenitor cells." These cells have a capability of limited self renewal and are constrained to committed development to various lymphoid and myeloid cells.

The term "hemangioblast" is intended to mean a pluripotent stem cell that gives rise to both hematopoietic stem cells and endothelial progenitor cells that can further differentiate into cells of all hematopoietic lineages (myeloid and lymphoid) as well as endothelial cells, respectively. The term "hematopoetic stem cell" is intended to mean a stem cell that gives rise to both myeloid and lymphoid cells. The term "myeloid" is intended to mean cells such as erythrocytes, platelets, neutrophils, monocytes, eosinophils, and basophils. The term "lymphoid" is intended to mean such cells as T cells, B cells and NK cells. The term "endothelial progenitor" is intended to mean a progenitor cell that gives rise to vascular endothelial cells. As used herein, the term "mesenchymal stem or progenitor cells" means that the progenitors give rise to cells of mesenchymal lineage; whereas "hematopoietic stem or progenitor cells" is intended to mean that the cells give rise to cells of the hematopoietic lineage.

The expanded stem cell population further comprises cells expressing the CD34 cell surface marker. The term "cell surface marker" is intended to mean a protein that is expressed on the surface of a cell, which can be detected using specific antibodies. Expression of cell surface marker CD34 correlates with stem and progenitor cell populations. $CD34^+$ $CD38^-$ cells are considered to be the earliest stem/progenitor cells. See, for example, Yu et al. (1996) *J. Formos. Med. Assoc.* 95:281. Thus, in one embodiment, the population of cells comprises $CD34^+$ cells wherein at least 90% to 100% of the cells do not express CD38.

Further, a subset of cells contained in the expanded stem cell population of the invention expresses increased amounts of CD34 on the cell surface. Those skilled in the art recognize that the cells with increased CD34 expression can be detected and isolated by any means including flow cytometric sorting, antibody panning, and the like. While not being limited to any method of detection, cells expressing increased amounts of CD34 on the cell surface are termed "$CD34^{br}$" cells because these cells tend to fluoresce brightly when stained with fluorescently labeled antibodies. By the term "bright" or it is intended to mean that the labeled cell surface marker of interest fluoresces more (using a flow cytometer or any other means known to skilled artisans) than other cells that also express the marker. Generally in flow cytometric analysis, one of skill in the art must first set a detection threshold for fluorescence. The detection threshold is then adjusted so that 97% or more of the cells do not fluoresce. Once the detection threshold is set, the fluorescence of cell population of interest is recorded. As used herein, the term "bright" or "$br$" is intended to mean that the cell population of interest fluoresces greater than about 2-fold, greater than about 5-fold, greater than about 10-fold, greater than about 20-fold, greater than about 30-fold, greater than about 40-fold, greater than about 50-fold, greater than about 60-fold, greater than about 70-fold, greater than about 80-fold, greater than about 90-fold, greater than about 100-fold, greater than about 200-fold, greater than about 300-fold, greater than about 400-fold, greater than about 500-fold, greater than about 600-fold, greater than about 700-fold, greater than about 800-fold, greater than about 900-fold, greater than about 1,000-fold, or more, compared to a control cell population. By using the term "dim" or "$dim$" it is intended that the cell population of interest expresses the marker but does not fluoresce at the level of the "bright" or "br" population. A cell is considered "positive for expression" when it expresses the marker of interest, whether a protein or a gene. Any method may be used to determine expression such as gene expression profiles, fluorescence activated cell sorting (FACS), and the like. The term "+" indicates that the cell is positive for expression as discussed supra. The term "−" indicates that the cell does not have detectable levels of expression of the marker of interest as determined by flow cytometry. For the purposes of the present invention, the $CD34^{br}$ cell population is defined as a population that has a measured fluorescence that is higher than that of the majority (peak of CD34 expression levels) of the freshly isolated $CD34^+$ cell population that is used to initiate the expansion culture or, in other embodiments, the majority of an expanded $CD34^{dim}$ population.

The antibodies used to detect various lineages may be conjugated to different fluorochromes. These include phycobiliproteins, e.g., phycoerythrin and allophycocyanins; fluorescein; and Texas red. Dead cells can also be detected using dyes that selectively accumulate in dead cells (e.g., propidium iodide and 7-amino actinomycin D). Cells can be collected in any appropriate medium, including medium comprising about 2% fetal calf serum (FCS) or 0.2% bovine serum albumin (BSA). See, for example, Fallon et al. (2003) *Br. J. Haematol.* 121:1, herein incorporated by reference.

The expanded stem and progenitor cells of the invention may also express combinations of cell markers of interest. Markers of interest include: CD31, CD33, CD34; CD42a; CD71; CD90; CD117 (c-Kit); CD133; CD135; HLA-DR; VEGF receptor; aldehyde dehydrogenase (ALDH); vWF (von Willebrand factor receptor); and any combinations of these markers. In some embodiments, a substantial proportion of the cells express the cell surface marker of interest. In some instances, the lack of expression of a cell surface marker defines stem cell populations, for example: CD3; CD14; CD19; CD16; CD38; CD42a; and any combinations of these markers.

Thus, in one embodiment, the population of cells comprises $CD34^{br}$ cells expanded in defined media such as a cytokine cocktail disclosed herein, wherein at least 10% to 100% of the cells express at least one marker selected from CD31, CD133, CD117, or a combination thereof. An increase in HLA-DR expression on adult bone marrow or peripheral blood derived cells generally correlates with lineage commitment in bone marrow and peripheral blood derived cells in contrast to cord blood hematopoietic stem cells where expression in high. See, for example, Yu et al. (1996) *J. Formos. Med. Assoc.* 95:281. Therefore, HLA-DR may be expressed in 0.1% to 100% of cells.

In some embodiments, the population of expanded cells comprises at least $CD34^{br}$ cells derived from umbilical cord blood and expanded in defined media such as those disclosed herein. $CD34^{br}$ cells may give rise to cells of the hematopoietic lineage, including, but not limited to, myeloid cells (such as granulocytes, dendritic cells, monocytes, platelets, megakaryocytes, and red bloods cells) and lymphoid cells (such as T cells, B cells, NK cells, and antigen presenting cells), endothelial cells (including endothelial cell progenitors and endothelium), and possibly give rise to cells in liver, and pancreas.

In one embodiment, the population of expanded cells is defined by fluorescence quantitation by flow cytometry using calibrated standardized phycoerythrin (PE)-conjugated beads and reagents (commercially available from Becton Dickinson Immunocytochemistry Systems, San Jose, Calif.). These bead standards can be used to measure the amount of fluorophore bound per cell. In this manner, fluorescence of PE beads can be measured in a fluorometer relative to known amounts of PE.

In one such embodiment, the Becton-Dickinson QuantiBRITE™ system of fluorescence quantitation is used (as described in "*QuantiBRITE™ White Paper: A New Standard for Fluorescence Quantitation*," available from Becton Dickinson Immunocytochemistry Systems, San Jose, Calif.). The QuantiBRITE™ system consists of QuantiBRITE™ PE Beads and QuantiQuest software. QuantiBRITE™ PE Beads include a set of four pre-calibrated bead levels in the form of a lyophilized pellet to calibrate the FL2 axis in terms of PE molecules. QuantiQuest is a quantitative calibration feature within CellQuest™ (Becton-Dickinson, San Jose, Calif.) acquisition software (version 3.1 and later) that calculates the linear function relating fluorescence to PE molecules. The PE copy number for a PE-stained cell is determined from the FL2 value of the cell and the linear regression equation.

The number of PE molecules per cell can be converted to antibody bound per cell (ABC) values if the PE:antibody ratio of the antibody conjugate is known. By "antibody bound per cell" or "ABC" is intended the number of a selected antibody of interest that have bound to cells in a selected cell population. In one embodiment, the PE:mAb ratio is 1:1 such that the number of PE molecules per cell is equivalent to the ABC value. The level of antibody binding can be detected using any suitable method known in the art. In one embodiment, the ABC value for the $CD34^{br}$ population and the total CD34+ population is detected using the QuantiBRITE™ system (commerically available from Becton Dickinson Immunocytochemistry Systems, San Jose, Calif.).

Having determined the ABC value, the number of antigens per cell can be determined given the antibody-to-antigen binding stoichiometry. Thus, for example, where the antibody-to-antigen binding stoichiometry is 1:1 for a PE-conjugated anti-CD34 antibody, the number of CD34 antigens is equivalent to the ABC value.

In one embodiment, the population of expanded cells comprises a population of $CD34^{br}$ cells that have an ABC value that is at least about 1.5-fold greater than that measured for the total CD34+ population (i.e., a $CD34^{br}$/total $CD34^+$ ABC ratio of at least 1.5). Thus, in some embodiments, the present invention provides a population of expanded cells comprising $CD34^{br}$ cells that have an ABC value that is at least about 1.5-fold greater, 1.6-fold greater, about 1.7-fold greater, about 1.8-fold greater, about 1.9-fold greater, about 2.0-fold greater, about 2.1-fold greater, about 2.2-fold greater, about 2.3-fold greater, about 2.4-fold greater, about 2.5-fold greater, about 2.6-fold greater, about 2.7-fold greater, about 2.8-fold greater, about 2.9-fold greater, about 3.0-fold greater, or about 3.1-fold greater than that measured for the total $CD34^+$ population.

Stem cell function can be assayed using both in vitro and in vivo methods. In vitro testing comprises culturing stem cells and progenitor cells in semi-solid medium and examining the resultant colonies. See, for example, Lu et al. (1993) *Blood* 81:41; Eaves, "Assays of Hematopoietic Progenitor Cells" in Williams (1995) *Hematology at L*22-6 ($5^{th}$ ed., E. Beutler et al eds.); Flores-Guzman et al. (2002) *Arch. Med. Res.* 33:107. In vivo testing generally involves grafting irradiated mice with the stem cells of interest. Cells can be recovered from these animals and examined for phenotype. Generally, cells that reconstitute more cell lineages are more primitive, and thus have great developmental potential. See, for example, Osawa et al. (1996) *Science* 273:242; Goodell et al. (1996) *J. Exp. Med.* 183:1797; Prosper et al. (2001) *J. Leukoc. Biol.* 69:307-316; Yu (1996) *J. Formos Med. Assoc.* 95:281-293; Bonner, et al., "The Blood and the Lymphoid Organs," in *Pathology* (Rubin et al., eds., 1999), pp. 1051-1061.

The expanded cells of the invention can be analyzed based on gene expression profiles. In this manner, the multilineage commitment potential can be determined. As used herein, an "expression profile" comprises one or more values corresponding to a measurement of the relative abundance of a gene expression product. Such values may include measurements of RNA levels or protein abundance. Thus, the expression profile can comprise values representing the measurement of the transcriptional state or the translational state of the gene. See, U.S. Pat. Nos. 6,040,138, 5,800,992, 6,020,135, 6,344,316, and 6,033,860, which are hereby incorporated by reference in their entirety.

The transcriptional state of a sample includes the identities and relative abundance of the RNA species, especially mRNAs present in the sample. Preferably, a substantial fraction of all constituent RNA species in the sample are measured, but at least a sufficient fraction to characterize the transcriptional state of the sample is measured. The transcriptional state can be conveniently determined by measuring transcript abundance by any of several existing gene expression technologies. Translational state includes the identities and relative abundance of the constituent protein species in the sample. As is known to those of skill in the art, the transcriptional state and translational state are related.

In some embodiments, the expanded cells of the invention change expression of genes that correlate with phenotype. For example, in one embodiment, the expression of genes differs between expanded $CD34^{br}$ and $CD34^{dim}$ cells. In some embodiments, greater than 15,000 of the gene transcription levels remain unchanged, over 500 are up-regulated and over 200 are down regulated, yielding over 700 "signature" gene profiles. In some embodiments, the level of expression of signature genes will vary over 2 fold between $CD34^{br}$ and $CD34^{dim}$ cells. For example, in some embodiments, CD133, which is a stem cell transcript marker, is increased over 2 fold in the $CD34^{br}$ versus $CD34^{dim}$ populations. In other embodiments, Delta-like 1 homologue (involved in inhibiting HSC differentiation) is increased over 2 fold in $CD34^{br}$ as compared to $CD34^{dim}$. In yet other embodiments, CSRP2, which participates in promoting smooth muscle cell proliferation and de-differentiation in the developing embryonic vasculature, is increased over 2 fold in $CD34^{br}$ as compared to $CD34^{dim}$. In some embodiments, DLK1, regulating homeostasis is increased at least 2 fold in $CD34^{br}$ as compared to $CD34^{dim}$. In some embodiments, STMN3, which has a role in cell proliferation, is increased at least 2 fold in $CD34^{br}$ as compared to $CD34^{dim}$. In other embodiments, CSRP2, a transcription factor promoting proliferation and de-differentiation is increased over 2.6 fold in $CD34^{br}$ as compared to $CD34^{dim}$. Increased expression of any one of these genes alone or in combination indicates that the cell is likely an earlier-stage progenitor cell.

In some embodiments, a relative decrease in a gene transcript in the $CD34^{br}$ versus $CD34^{dim}$ population is indicative of an earlier-stage multipotential stem or progenitor cell population. For example in some embodiments, CEBPD (an adipocyte differentiation marker) is decreased greater than 2 fold in the $CD34^{br}$ versus $CD34^{dim}$ population; EMP2 (an epithelial cell differentiation marker) is decreased greater than 2 fold in the $CD34^{br}$ versus $CD34^{dim}$ population; CSFIR (a myeloid cell differentiation marker) is decreased greater than 3 fold in the $CD34^{br}$ versus $CD34^{dim}$ population; DCNP1 (a dendritic cell differentiation marker) is decreased greater than 3 fold in the $CD34^{br}$ versus $CD34^{dim}$ population; PRG1 (a hematopoietic cell proliferation marker) is decreased greater than 4 fold in the $CD34^{br}$ versus $CD34^{dim}$ population; CXCR4 (the SDF1 receptor involved in leucopoiesis) is decreased greater than 2 fold in the $CD34^{br}$ versus $CD34^{dim}$ population; IL-10RA (a mediator of inhibition of T cell and macrophage proliferation) is decreased greater than 3 fold in the $CD34^{br}$ versus $CD34^{dim}$ population; EB12 (a receptor induced by EBV lymphocyte function) is decreased greater than 3 fold in the $CD34^{br}$ versus $CD34^{dim}$ population; or some combination thereof.

In some embodiments, $CD34^{dim}$ cells show up-regulation of transcription of such genes as HCK (involved in hematopoietic differentiation) increasing greater than 2 fold as compared to $CD34^{br}$; LYZ (a monocytes macrophage marker) increasing greater than 9 fold as compared to $CD34^{br}$; IL-8 (a monocyte marker) increasing greater than 2 fold as compared to $CD34^{br}$; LGALS1 (a differentiation and apoptosis marker) increasing greater than 3 fold as compared to $CD34^{br}$; PLA2G7 (a platelet regulation marker) increasing greater than 4 fold as compared to $CD34^{br}$; CLC (an eosinophil and basophil marker) increasing over 4 fold as compared to $CD34^{br}$; RNASE2 (an eosinophil marker) increasing over 3 fold as compared to $CD34^{br}$; RNASE 3 (an eosinophil marker) increasing over 2 fold as compared to $CD34^{br}$;

S100A12 or calgranulin (a neutrophil marker) increasing greater than 3 fold as compared to $CD34^{br}$; AOAH (a neutrophil marker) increasing greater than 3 fold as compared to $CD34^{br}$; MPO (a neutrophil marker) increasing over 3 fold as compared to $CD34^{br}$; CTSG (a neutrophil monocytes marker) increasing over 2 fold as compared to $CD34^{br}$; S100A9 or calgranulin B (a macrophage marker) increasing over 9 fold as compared to $CD34^{br}$; SCYA13 (monocyte chemoattractant protein 4) increasing over 5 fold as compared to $CD34^{br}$; SCYA2 (a macrophage derived marker) increasing over 5 fold as compared to $CD34^{br}$; SCYB13 (a B lymphocyte chemoattractant) increasing over 4 fold as compared to $CD34^{br}$; CD14 increasing over 5 fold as compared to $CD34^{br}$; and combinations thereof.

In some embodiments, the expanded cells of the invention express genes differentially over time in culture. For example, in some embodiments $CD34^{br}$ cells show decreasing amounts of CD164 transcripts; SELL transcripts; SDFR1 transcripts; and combinations thereof over time. In other embodiments, $CD34^{br}$ cells express increasing amounts of FADD over time. In some embodiments, the $CD34^{dim}$ population expresses increased FADD transcripts; increased ITGB2 transcripts; increased S100A9 transcripts; and combinations thereof over time.

In one embodiment of the invention, microarrays are used to measure the values to be included in the expression profiles. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, the Experimental section. See also, U.S. Pat. Nos. 6,040,138, 5,800,992, 6,020,135, 6,033,860, and 6,344,316, which are incorporated herein by reference. High-density oligonucleotide arrays are particularly useful for determining the gene expression profile for a large number of RNAs in a sample.

"Array" is intended to mean a solid support or substrate with peptide or nucleic acid probes attached to the support or substrate. Arrays typically comprise a plurality of different nucleic acid or peptide capture probes that are coupled to a surface of a substrate in different, known locations. These arrays, also described as "microarrays" or colloquially "chips," have been generally described in the art, for example, in U.S. Pat. Nos. 5,143,854, 5,445,934, 5,744,305, 5,677,195, 6,040,193, 5,424,186, 6,329,143, and 6,309,831 and Fodor et al. (1991) *Science* 251:767-77, each of which is incorporated by reference in its entirety.

Through the use of statistically designed experiments, defined combinations of agents were identified for ex vivo expansion of stem and progenitor cells of the present invention. In one embodiment, the defined combinations comprise at least 5, at least 6, at least 7, at least 8, at least 9, at least 10, at least 11, at least 12, at least 13, at least 14, at least 15, or at least 16 cytokines. Defined combinations of the present invention can comprise: fibronectin, stromal cell derived factor 1α (SDF-1α), IL-6, stem cell factor (SCF), IL-5, brain-derived neurotrophic factor (BDNF), platelet-derived endothelial cell growth factor (PD-ECGF), IL-11, IL-3, erythropoietin (EPO), Flt-3/Flk-2 ligand, bone morphogenic protein (BMP-4), thrombospondin, insulin-like growth factor (IGF-1), basic fibroblast growth factor (bFGF), angiotensin, platelet derived growth factor having both the A chain and B chain heterodimer (PDGF-AB), transforming growth factor beta1 (TGF-β1), granulocyte macrophage colony stimulating factor (GM-CSF), vascular endothelial growth factor (VEGF), epidermal growth factor (EGF), macrophage colony stimulating factor (M-CSF), and monocyte chemotactic protein-1/CCL2 (MCP-1), placental growth factor (PlGF), hematopoietic adhesion peptide comprising the amino acid sequence VTCG (SEQ ID NO:1), TNF related activation induced cytokine (TRANCE), and granulocyte colony stimulating factor (G-CSF).

In one embodiment, the defined cytokine cocktail is termed "G2" and comprises a combination of fibronectin, SDF-1α, IL-6, SCF, IL-5, BDNF, PD-ECGF, IL-11, IL-3, EPO, Flt-3/Flk-2 ligand, BMP-4, thrombospondin, IGF-1, and bFGF.

Less than 1% of the G2-expanded population comprises T-cells (CD3), B-cells (CD19) or mature granulocytes, NK lymphocytes, or macrophages (CD16) after expansion; less than 10% of the population comprises monocytes (CD14), differentiating hematopoietic cells (CD38), and platelets or megakaryocytes (CD42a) after expansion. Greater than 25% of the population comprises endothelial cells, platelets, leukocytes or their precursors (CD31), myeloid progenitor cells (CD33), hematopoietic stem and progenitor cells (CD34), proliferating cells and erythroid precursors (CD71). Greater than 10% of the cells comprise neural stem cells (CD133) and $CD34^{br}$ stem and progenitor cells. In one embodiment, the G2 expanded cell populations comprise stem cell populations wherein less than 1% of the cells express CD3, less than 10% of the cells express CD14, less than 1% of the cells express CD16, less than 1% of cell express CD19, greater than 80% of the cells express CD31, greater than 60% of the cells express CD33, greater than 25% of the cells express CD34, less than 5% of the cells express CD38, less than 10% of the cells express CD42a, greater than 40% of the cells express CD71, greater than 15% of the cells express CD133, greater than 10% of the cells express as $CD34^{br}$, and combinations thereof.

In another embodiment, the defined cytokine cocktail is termed "F2" and comprises angiotensin, IL-6, SCF, BDNF, IL-3, PDGF-AB, BMP-4, TGF-β1, thrombospondin, GM-CSF, VEGF, EGF, bFGF, M-CSF, and MCP-1.

Less than 1% of the F2-expanded population comprises T-cells (CD3), B-cells (CD19) or mature granulocytes, NK lymphocytes, or macrophages (CD16) after expansion; less than 15% of the population comprises monocytes (CD14), differentiating hematopoietic cells (CD38), and platelets or megakaryocytes (CD42a) after expansion; greater than 10% of the population comprises endothelial cells, platelets, leukocytes or their precursors (CD31), myeloid progenitor cells (CD33), hematopoietic stem and progenitor cells (CD34), proliferating cells and erythroid precursors (CD71); greater than 2% of the cells comprise neural stem cells (CD133) and $CD34^{br}$ stem and progenitor cells. In one embodiment, the F2-expanded cell populations comprise stem cell populations wherein less than 1% of the cells express CD3, less than 15% of the cells express CD14, less than 1% of the cells express CD16, less than 1% of cell express CD19, greater than 50% of the cells express CD31, greater than 50% of the cells express CD33, greater than 15% of the cells express CD34, less than 5% of the cells express CD38, less than 10% of the cells express CD42a, greater than 40% of the cells express CD71, greater than 1% of the cells express CD133, greater than 7% of the cells express as $CD34^{br}$, and combinations thereof.

In a further embodiment, the defined cytokine cocktail is termed "D6" and comprises PlGF, SDF-1α, IL-6, SCF, IL-5, BDNF, IL-11, IL-3, EPO, PDGF-AB, Flt-3/Flk-2 ligand, hematopoietic adhesion peptide comprising the amino acid sequence VTCG (SEQ ID NO:1), TRANCE, GM-CSF, VEGF, and G-CSF.

Less than 1% of the D6-expanded population comprises T-cells (CD3), B-cells (CD19) or mature granulocytes, NK lymphocytes, or macrophages (CD16) after expansion; less than 10% of the population comprises monocytes (CD14), differentiating hematopoietic cells (CD38), and platelets or megakaryocytes (CD42a) after expansion; greater than 20% of the population comprises endothelial cells, platelets, leukocytes or their precursors (CD31), myeloid progenitor cells (CD33), hematopoietic stem and progenitor cells (CD34), proliferating cells and erythroid precursors (CD71); greater than 5% of the cells comprise neural stem cells (CD133) and CD34$^{br}$ stem and progenitor cells. In one embodiment, the D6-expanded cell populations comprise stem cell populations wherein less than 1% of the cells express CD3, less than 10% of the cells express CD14, less than 1% of the cells express CD16, less than 1% of cells express CD19, greater than 80% of the cells express CD31, greater than 60% of the cells express CD33, greater than 20% of the cells express CD34, less than 5% of the cells express CD38, less than 5% of the cells express CD42a, greater than 50% of the cells express CD71, greater than 10% of the cells express CD133, greater than 5% of the cells express as CD34$^{br}$, and combinations thereof.

In a further embodiment, the defined cytokine cocktail is termed "F2N" and comprises BDNF, bFGF, EPO, fibronectin, Flt-3/Flk-2 ligand, IGF-1, IL-11, IL-3, IL-5, SCF, TGF-β1, G-CSF, and GM-CSF.

In a further embodiment, the defined cytokine cocktail is termed "F4" and comprises bFGF, EPO, Flt-3/Flk-2 ligand, IL-11, IL-6, PD-ECGF, thrombospondin, and thrombopoetin (Tpo).

In a further embodiment, the defined cytokine cocktail is termed "G8" and comprises BDNF, bFGF, Flt-3/Flk-2 ligand, IL-3, IL-6, PD-ECGF, SCF, G-CSF, leukemia inhibitory factor (LIF), and stem cell growth factor-α (SCGF-α).

These defined cytokine combinations may be added to a base nutritive medium to provide a culture medium suitable for maintaining or expanding cord blood derived and/or other cells. Any nutritive medium suitable for the culture of mammalian cells, particularly stem cells, may be used, for example, Stemline™ (Sigma-Aldrich, MO). The final concentration of these cytokines in the nutritive media can range from 1 femtogram/ml to 1 picogram/ml to 1 nanogram/ml to 1 milligram/ml. In some embodiments, the concentration of any one of the cytokines can be 1 pg/ml, 5 pg/ml, 10 pg/ml, 15 pg/ml, 20 pg/ml, 25 pg/ml, 30 pg/ml, 35 pg/ml, 40 pg/ml, 45 pg/ml, 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, 100 pg/ml, 110 pg/ml, 120 pg/ml, 130 pg/ml, 140 pg/ml, 150 pg/ml, 160 pg/ml, 170 pg/ml, 180 pg/ml, 190 pg/ml, 200 pg/ml, 210 pg/ml, 220 pg/ml, 230 pg/ml, 240 pg/ml, 250 pg/ml, 260 pg/ml, 270 pg/ml, 280 pg/ml, 290 pg/ml, 300 pg/ml, 310 pg/ml, 320 pg/ml, 330 pg/ml, 340 pg/ml, 350 pg/ml, 360 pg/ml, 370 pg/ml, 380 pg/ml, 390 pg/ml, 400 pg/ml, 410 pg/ml, 420 pg/ml, 430 pg/ml, 440 pg/ml, 450 pg/ml, 460 pg/ml, 470 pg/ml, 480 pg/ml, 490 pg/ml, 500 pg/ml, 510 pg/ml, 520 pg/ml, 530 pg/ml, 540 pg/ml, 550 pg/ml, 560 pg/ml, 570 pg/ml, 580 pg/ml, 590 pg/ml, 600 pg/ml, 610 pg/ml, 620 pg/ml, 630 pg/ml, 640 pg/ml, 650 pg/ml, 660 pg/ml, 670 pg/ml, 680 pg/ml, 690 pg/ml, 700 pg/ml, 710 pg/ml, 720 pg/ml, 730 pg/ml, 740 pg/ml, 750 pg/ml, 760 pg/ml, 770 pg/ml, 780 pg/ml, 790 pg/ml, 800 pg/ml, 810 pg/ml, 820 pg/ml, 830 pg/ml, 840 pg/ml, 850 pg/ml, 860 pg/ml, 870 pg/ml, 880 pg/ml, 890 pg/ml, 900 pg/ml, 910 pg/ml, 920 pg/ml, 930 pg/ml, 940 pg/ml, 950 pg/ml, 960 pg/ml, 970 pg/ml, 980 pg/ml, 990 pg/ml, 1 ng/ml, 1.5 ng/ml, 2 ng/ml, 2.5 ng/ml, 3 ng/ml, 3.5 ng/ml, 4 ng/ml, 4.5 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 ng/ml, 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml, 110 ng/ml, 120 ng/ml, 130 ng/ml, 140 ng/ml, 150 ng/ml, 160 ng/ml, 170 ng/ml, 180 ng/ml, 190 ng/ml, 200 ng/ml, 210 ng/ml, 220 ng/ml, 230 ng/ml, 240 ng/ml, 250 ng/ml, 260 ng/ml, 270 ng/ml, 280 ng/ml, 290 ng/ml, 300 ng/ml, 310 ng/ml, 320 ng/ml, 330 ng/ml, 340 ng/ml, 350 ng/ml, 360 ng/ml, 370 ng/ml, 380 ng/ml, 390 ng/ml, 400 ng/ml, 410 ng/ml, 420 ng/ml, 430 ng/ml, 440 ng/ml, 450 ng/ml, 460 ng/ml, 470 ng/ml, 480 ng/ml, 490 ng/ml, 500 ng/ml, 510 ng/ml, 520 ng/ml, 530 ng/ml, 540 ng/ml, 550 ng/ml, 560 ng/ml, 570 ng/ml, 580 ng/ml, 590 ng/ml, 600 ng/ml, 610 ng/ml, 620 ng/ml, 630 ng/ml, 640 ng/ml, 650 ng/ml, 660 ng/ml, 670 ng/ml, 680 ng/ml, 690 ng/ml, 700 ng/ml, 710 ng/ml, 720 ng/ml, 730 ng/ml, 740 ng/ml, 750 ng/ml, 760 ng/ml, 770 ng/ml, 780 ng/ml, 790 ng/ml, 800 ng/ml, 810 ng/ml, 820 ng/ml, 830 ng/ml, 840 ng/ml, 850 ng/ml, 860 ng/ml, 870 ng/ml, 880 ng/ml, 890 ng/ml, 900 ng/ml, 910 ng/ml, 920 ng/ml, 930 ng/ml, 940 ng/ml, 950 ng/ml, 960 ng/ml, 970 ng/ml, 980 ng/ml, 990 ng/ml, 1000 ng/ml. Those skilled in the art recognize that these cytokines may be concentrated and, in some instances, lyophilized before addition to the nutritive medium to obtain the examples of final concentrations listed above. Those skilled in the art also recognize that the mass weight added to culture will depend on the specific biological activity of the cytokine preparation. Bioassays to determine the biological potency of cytokines are well known in the art. Therefore, where the biological activity is correlated to a mass weight, then biological "units" as defined by the assay are used.

The methods of the invention comprise culturing or expanding stem cells from a stem cell source in a nutritive media containing a cytokine cocktail. Methods of culture of cells are well known in the art. See for example Waymouth, C., *Cell Culture Methods for Molecular and Cell Biology*, Vol. 1, Barnes et al., eds. (1984 New York). By "cell-culture" is intended to mean the maintenance of cells in an artificial in vitro environment. It is to be understood that the term "cell culture" is a generic term and may be used to encompass the cultivation not only of individual cells but also tissues, organ systems, or whole organisms. In some embodiments, cells derived from a stem cell source are placed in a culture vessel containing the nutritive medium. The medium may contain the cytokine combination, or the cytokines can be added later. Cells are then incubated with the cytokine combination at a temperature suitable for cell growth (for some embodiments about 37° C.), for at least 24 hours, at least 48 hours, at least 72 hours, at least 96 hours, or longer. Cells may be harvested in any manner known in the art including but not limited to centrifugation for collecting non-adherent cells, trypsinizing adherent cells, or scraping cells from the surface.

Stromal cells play an important role for the proliferation and differentiation of hematopoietic cells in the bone marrow. See for example, Verfaillie et al. (1999) *Hematol.*, 4:321; Wright et al. (1986) *Prog. Clin. Biol. Res.* 211:135-157; and, Allen et al. (1984) *Exp. Hematol.* 12(7):517-521; Dexter et al. (1977) *Biomedicine* 27(9-10):344-349. Thus, a stromal feeder layer established in cultures of bone marrow derived hematopoietic cell preparations or even murine cultured cells such as AFT024 can sometimes be utilized to maintain hematopoietic stem and progenitor cells ex vivo. See, for example, Nolta et al. (2002) *Leukemia* 16(3):352-361. Thus, in some embodiments, expansion of the cells of the invention may comprise contacting stem cells derived with stromal feeder cells. In other embodiments, stromal cells are derived from cord blood when unfractionated white blood cells (total nucleated cells, TNCs) from a stem cell source are cultured in the cytokine cocktails disclosed herein. Though isolation and culture of stromal cells from bone marrow can be accomplished using methods known in the art, only a few reports exist that describe how to derive stromal cells from an umbilical cord blood source (see, for example, Lee et al. (2005) *Int. J. Hematol.* 81:126-130; Yang et al. (2004) *Cytotherapy* 6:476-486). In accordance with the methods of the present invention, expansion of adherent stromal cells is obtained by culturing umbilical cord blood-derived total nucleated cells in a cytokine cocktail disclosed herein, particularly the G2 medium described above. Stromal cells derived from culture in cytokine cocktails may be combined with the expanded $CD34^{br}$ cell populations for any of the methods described herein. In some embodiments, the expanded stromal cells comprise mesenchymal stem cells capable of giving rise to at least one or more cell types of mesenchymal origin.

Alternative hematopoietic stem and progenitor cells sources, for example cord blood, mobilized peripheral blood, or placenta, will not automatically supply a stromal feeder layer. In addition, cells for therapeutic applications must be maintained in well-defined cultures with no risk of immunogenic or infectious consequences for the cell recipient. For therapeutic applications, it is not desirable to allow direct contact between the therapeutic cells and undefined feeder layers. Alternative culture systems have been studied and are known in the art. See, for example, Verfaillie et al. (1999) *Hematol.* 4(4):321-333.

Thus, undefined stromal feeder layers are not generally desirable, in particular in cases where an autologous transplant is not possible due to the patient's disease. Therefore, the present invention provides well-controlled and well-defined culture conditions for the proliferation of stem and progenitor cells, including stroma free culture. The present invention further provides cytokine supplementation that sustains SPC growth over time such that the amount of cells does not drop below the input level.

The cells used in culture can include cells derived from any stem cell source, such as umbilical cord blood, peripheral blood, fetal liver, placenta, embryonic stem cells, or bone marrow. These samples may be fresh, frozen, or refrigerated. Methods of freezing cells are well known in the art. See for example, Doyle et al. (1995) *Cell & Tissue Culture: Laboratory Procedures* (John Wiley & Sons, Chichester).

Cryopreservation of stem cells prior to culture or cryopreservation of expanded cells disclosed herein may be carried out according to known methods. For example, cells may be suspended in a "freezing medium" such as, for example, culture medium further comprising 10% dimethylsulfoxide (DMSO), with or without 5-10% glycerol, at a density, for example, of about $0.5-4\times10^6$ cells/ml. The cells are dispensed into glass or plastic vials, which are then sealed and transferred to a freezing chamber of a programmable or passive freezer. The optimal rate of freezing may be determined empirically. For example, a freezing program that gives a change in temperature of $-1°$ C./min through the heat of fusion may be used. Once vials containing the cells have reached $-80°$ C., they are transferred to a liquid nitrogen storage area. Cryopreserved cells can be stored for a period of years.

In some embodiments, freshly isolated cells from any stem cell source may be cryopreserved to constitute a bank of cells, portions of which can be withdrawn by thawing and then used to produce the expanded cells of the invention as needed. Thawing should generally be carried out rapidly, for example, by transferring a vial from liquid nitrogen to a $37°$ C. water bath. The thawed contents of the vial should be immediately transferred under sterile conditions to a culture vessel containing an appropriate medium such as nutritive medium. Once in culture, the cells may be examined daily, for example, with an inverted microscope to detect cell proliferation, and subcultured as soon as they reach an appropriate density.

Cells may be withdrawn from a cell bank as needed, and used for the production of new stem cells or tissue either in vitro, for example, as a three dimensional scaffold culture, as described below, or in vivo, for example, by direct administration of cells to the site where tissue reconstitution or repair is needed. As described herein, the expanded cells of the invention may be used to reconstitute or repair tissue in a subject where the cells were originally isolated from that subject's own blood or other tissue (i.e., autologous cells). Alternatively, the expanded cells disclosed herein may be used as ubiquitous donor cells to reconstitute or repair tissue in any subject (i.e., heterologous cells).

Prior to culture, a large proportion of terminally differentiated cells may be removed from a stem cell source by negatively selecting differentiated cells. For example, large numbers of lineage-committed cells can be removed by selective magnetic bead separations. In some embodiments, at least about 80%, usually at least about 70% of the differentiated cells will be removed prior to culture.

Cultured SPC can be further characterized using any method known in the art. Generally, stem cells are contacted with monoclonal antibodies directed to cell surface antigens and either positively or negatively selected. Such techniques for selection are well known in the art and include sorting by immunomagnetic beads, by complement mediated lysis, by "panning" with antibody attached to a solid matrix, agglutination methods, magnetic activated cell sorting (MACS), or FACS.

The expanded cells of the invention have broad application in treating and ameliorating disease and injury. The expanded cells of the invention are useful in many therapeutic applications including repairing, reconstituting, and regenerating tissue as well as gene delivery. The cells of the invention can comprise both lineage committed and uncommitted cells; thus, both cell types can be used together to accomplish multiple therapeutic goals, even simultaneously in some embodiments. For example, in some embodiments, the expanded cells of the invention can be used to treat immunodeficiencies or be used as stem cell transplants or be used in stem cell grafts either in suspension or on a support scaffold.

The expanded cells of the invention can be placed in a carrier medium before administration. For infusion, expanded cells of the invention can be administered in any physiologically acceptable medium, normally intravascularly, including intravenously, although they may also be introduced into other convenient sites such as into the bone marrow, where the cells may find an appropriate site for regeneration and differentiation. Usually, at least $1\times10^5$ cells/kg, at least $5\times10^5$ cells/kg, at least $1\times10^6$ cells/kg, $2\times10^6$ cells/kg, $3\times10^6$ cells/kg, $4\times10^6$ cells/kg, $5\times10^6$ cells/kg, $6\times10^6$ cells/kg, $7\times10^6$ cells/kg, $8\times10^6$ cells/kg, $9\times10^6$ cells/kg, $10\times10^6$ cells/kg, or more will be administered. See, for example, Ballen et al. (2001) *Transplantation* 7:635-645. The cells may be introduced by any method including injection, catheterization, or the like. If desired, additional drugs or growth factors can be co-administered. Drugs of interest include 5-fluorouracil and growth factors including cytokines such as IL-2, IL-3, G-CSF, M-CSF, GM-CSF, IFNγ, and EPO.

Administered cells may also comprise a mixture of cells of the invention and additional cells of interest. Cells of interest include differentiated liver cells, differentiated cardiac muscle, differentiated pancreatic cells, or precursors to these differentiated cells and the like. These combinations are particularly useful when the expanded cells of the invention are seeded on a three-dimensional scaffold as disclosed herein.

In some embodiments, the expanded cells of the population can be used to modulate the immune response. For example, because progenitor and stem cells can develop into lymphoid cells, antigens may be loaded into these cells. As they develop, the can induce tolerance or immunity to specific antigens depending on the therapeutic application and antigen.

In some embodiments, the expanded cells of the invention are useful in reconstituting bone marrow function, for example where bone marrow has been ablated such as in cancer radiation or chemotherapy. Examples of diseases where bone marrow function is impaired include, but are not limited to, the class of leukemias, the class of anemias such as sickle cell, thalassemia, and Von Willebrand's disease, the class of lymphomas including Hodgkin's disease and multiple myeloma, the class of solid organ cancer such as lung, breast, testicular, ovarian, and colon cancer. In some embodiments, stem cells from a patient may be removed, expanded, and re-introduced. In these cases, the stem cell source for expansion includes mobilized peripheral blood and bone marrow. After expansion, these cells can be sorted and re-introduced to reduce the chance of returning cancer cells to the recipient, thereby improving outcomes for autologous stem cell transplants.

Treatments are not limited to the more traditional uses for hematopoietic stem cells. As described herein, the expanded stem and progenitor cells of the invention can differentiate into both hematopoietic and mesenchymal lineages. See, for example, Otani et al. (2002) *Nat. Med.* 8:1004. Therefore, in some embodiments, the expanded cell population of the invention can be used to repair and reconstitute damaged or diseased mesenchymal tissues, such as the heart, the pancreas, the liver, bone, cartilage, endothelium, nerves, astrocytes, dermis, and the like. Once the expanded cells home or are placed in the site of injury, they can differentiate to form new tissues and supplement organ function. In some embodiments, the cells are used to promote vascularization and, therefore, improve oxygenation and waste removal from tissues. In these embodiments, the expanded cells of the invention can be used to increase function of differentiated tissues and organs such as the ischemic heart as in cardiac failure or ischemic nerves as in stroke. Therefore, the stem cells of the invention are useful in any disease where cellular function or organ function has been decremented.

The expanded cells of the invention can be used for implantation by contacting the cells with a tissue-engineered construct prior to grafting. The construct containing these cells is then implanted into a host in need of such a graft. The cells of the invention are particularly useful for promoting vasculogenesis and angiogenesis in the graft, thereby facilitating oxygenation and waste removal, and decreasing the risk of ischemic necrosis and inflammation in the graft. In some embodiments, the tissue-engineered construct of the invention comprises at least vasculature promoting stem cells, differentiated cells on a three-dimensional biocompatible scaffold, and thereby performing at least one physiological function of the organ to be repaired or replaced. The expanded cells of the invention are particularly useful as vasculature promoting stem cells. "Vascularization promoting" or "vasculature promoting" is intended to mean promoting the growth of new vessels (vasculogenesis) or inducing outgrowth from existing vessels (angiogenesis), or any combination thereof.

"Differentiated cells" is intended to mean cells that are committed to restricted tissue development. In some embodiments, the expanded cells of the invention may comprise both lineage committed and uncommitted cells. Thus, in some constructs the stem cells may give rise to both the differentiated tissue and act as the source for the vasculature promoting cells. In other embodiments, the source of differentiated tissues may comprise cells or tissue from the intended graft recipient or another donor. The cell or tissue source may be differentiated prior to implantation. For example, pancreatic beta cells can be differentiated using conditions described for embryoid body formation as detailed in Itskovich-Eldor et al. (2000) *Mol. Med.* 6:88 and Assady et al. (2001) *Diabetes* 50.

Vasculature promoting cells that are combined with the differentiated cells may comprise for example, $CD34^{br}$ cells derived from any stem cell source including umbilical cord blood, endothelial progenitor cells either freshly isolated or differentiated in vitro from $CD34^{br}$ cells, freshly isolated stem cells from any stem cell source, and cells from any source selected for expression of the cell surface markers CD34, CD34 coexpressed with CD133, and CD34 co-expressed with CD31. In some embodiments, the vasculature promoting cells are contacted with angiogenic growth factors such as VEGF and bFGF. The cells can be contacted with angiogenic growth factors prior to or after seeding onto the scaffold before engrafting the construct into a damaged organ. In some embodiments, cytokine impregnated polymers can release the VEGF and bFGF over time. In other embodiments, the scaffold may be programmed to drive expansion and proliferation of seeded cells. See, for example, U.S. Patent Application Publication No. 20040063206. In other embodiments, microspheres may be contacted with the vasculature promoting stem cells and placed at a target site. Microsphere based scaffolds are well known in the art. See, for example, Mahoney and Saltzman (2001) *Nature Biotech.* 19:934.

"Supplementing a damaged organ" is intended to mean increasing, enhancing, and improving the function of an organ that is operating at less than optimum capacity. The term is used to refer to a gain in function so that the organ is operating at a physiologically acceptable capacity for that subject. For example, the physiological acceptable capacity for an organ from a child, e.g., a kidney or heart, would be different from the physiological acceptable capacity of an adult, or an elderly patient. The entire organ, or part of the organ can be supplemented. Preferably the supplementation results in an organ with the same physiological response as a native organ. In one embodiment, an organ is supplemented in capacity when it is functioning to at least at about 10% of its natural capacity.

When the three-dimensional biocompatible scaffold, after contact with vasculature promoting expanded cells of the invention, is brought into contact with a host tissue at a target site (e.g., within the organ) or where the organ tissue is grown on the scaffold prior to implantation, the graft is able to grow and proliferate within the target site and replace or supplement the depleted activity of the organ. The construct can be added at a single location in the host. Alternatively, a plurality of constructs can be created and added to multiple sites in the host.

The term "target site" as used herein refers to region in the host or organ that requires replacement or supplementation. The target site can be a single region in the organ or host, or can be multiple regions in the organ or host. In some embodiments, the supplementation or replacement results in the same physiological response as a normal organ.

The shape and dimensions of the scaffold are determined based on the organ being replaced or supplemented, and the type of scaffold material being used to create the construct. For example, if a polymeric scaffold is used for kidney replacement or supplementation, the dimension of the polymeric scaffold can vary in terms of width and length of the polymeric scaffold. One of skill in the arts recognizes that the size and dimensions of the polymeric scaffold will be determined based on the area of the organ being replaced or supplemented.

The term "decellularized" or "decellularization" as used herein refers to a biostructure (e.g., an organ, or part of an organ), from which the cellular and tissue content has been removed leaving behind an intact acellular infrastructure. The process of decellularization removes the specialized tissue, leaving behind the complex three-dimensional network of connective tissue. The connective tissue infrastructure is primarily composed of collagen. The decellularized structure provides a matrix material onto which different cell populations can be infused. Decellularized biostructures can be rigid, or semi-rigid, having an ability to alter their shapes. Culture and construction of decellularized biostructures can be performed, for example, as described in U.S. Pat. No. 6,479,064, which is herein incorporated by reference in its entirety.

The tissue-engineered constructs of the present invention are created using scaffold materials as the substrate onto which cells are deposited, and on which cells are grown and adhere.

The invention provides a method of forming tissue-engineered constructs using a scaffold material that supports the maturation, development and differentiation, of additional cultured cells in vitro to form components of adult tissues analogous to their in vivo counterparts. The scaffold allows optimum cell-cell interactions, thereby allowing a more natural formation of cellular phenotypes and a tissue microenvironment. The scaffold also allows cells to continue to grow actively, proliferate and differentiate to produce a tissue engineered construct that is also capable of supporting the growth, proliferation and differentiation of additional cultured cells populations, if needed.

Cells grown on the scaffold materials, in accordance with the present invention, may grow in multiple layers, forming a cellular structure that resembles physiologic conditions found in vivo. The scaffold can support the proliferation of different types of cells and the formation of a number of different tissues. Examples include, but are not limited to, kidney, heart, skin, liver, pancreas, adrenal and neurological tissue, as well as tissues of the gastrointestinal and genitourinary tracts, and the circulatory system.

The seeded scaffold can be used in a variety of applications. For example, the scaffold can be implanted into a subject. Implants, according to the invention, can be used to replace or supplement existing tissue, for example, by treating a subject with a pancreatic disorder by replacing or supplementing the natural pancreas. The subject can be monitored after implantation for amelioration of the pancreatic disorder.

In some embodiments, the scaffold is a polymeric material. Examples of suitable polymers include, but are not limited to, alginate, hyaluronate, collagen, poly(alpha esters) such as poly(lactate acid), poly(glycolic acid), polyorthoesters and polyanhydrides and their copolymers, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyestercarbonate, polyether, polyetheretherketone, polyetherimide, polyetherketone, polyethersulfone, polyethylene, polyfluoroolefin, polylmide, polyolefin, polyoxadiazole, polyphenylene oxide, polyphenylene, sulfide, polypropylene, polystyrene, polysulfide, polysulfone, polytetrafluoroethylene, polythioether, polytriazole, polyurethane, polyvinylidene fluoride, regenerated cellulose, urea-formaldehyde, or copolymers or physical blends of these materials.

Polymers, such as polyglycolic acid, are suitable biocompatible structures for producing an organ augmenting structure. The biocompatible polymer may be shaped using methods such as, solvent casting, compression molding, filament drawing, meshing, leaching, weaving and coating.

Other scaffold materials include biodegradable polymers including polyglycolic and acid polymers (PGA), polylactic acid polymers (PLA), polysebacic acid polymers (PSA), poly(lactic-co-glycolic) acid copolymers (PLGA), poly(lactic-co-sebacic) acid copolymers (PLSA), poly(glycolic-co-sebacic) acid copolymers (PGSA), and polyhydroxyalkanoate (PHA). PHAs and their production are described in, for example, PCT Publication Nos. WO 99/14313, WO 99/32536 and WO 00/56376. Combinations of biodegradable polymers, e.g., PGA and PLGA, can also be used.

Other biodegradable polymers useful in the present invention include polymers or copolymers of caprolactones, carbonates, amides, amino acids, orthoesters, acetals, cyanoacrylates and degradable urethanes, as well as copolymers of these with straight chain or branched, substituted or unsubstituted, alkanyl, haloalkyl, thioalkyl, aminoalkyl, alkenyl, or aromatic hydroxy- or di-carboxylic acids. In addition, the biologically important amino acids with reactive side chain groups, such as lysine, arginine, aspartic acid, glutamic acid, serine, threonine, tyrosine and cysteine, or their enantiomers, may be included in copolymers with any of the aforementioned materials.

Since this invention employs cell-seeded scaffolds for preparing therapeutic tissues, it is necessary for the scaffold to be biocompatible and conducive to cell attachment and subsequent tissue growth. Thus, surface properties can be modified to suit the intended application, without altering other properties of the scaffold such as its mechanical strength or thermal properties. Useful surface modifications could include, for example, changes in chemical group functionality, surface charge, hydrophobicity, hydrophilicity, and wettability. For example, cellular adhesion can be facilitated by attaching or coating the surface with a bioactive compound or peptide that promotes cellular attachment. The coating or bioactive compound may be attached to the surface either covalently or non-covalently. Such skills are well known in the art.

Sterilization is performed prior to seeding the scaffold with cells. Heat sterilization is often impractical since the heat treatment could deform the device, especially if the materials have a melting temperature below that required for the heat sterilization treatment. Thus, cold ethylene oxide gas can be used as a sterilizing agent in some embodiments. Alternatively, gamma radiation or electron-beam sterilization can be used.

Suitable growth conditions and media for cells in culture are well known in the art. Cell culture media typically comprise essential nutrients, but also optionally include additional elements (e.g., growth factors, salts and minerals) that may be customized for the growth and differentiation of particular cell types.

The polymeric matrix can be fabricated to have a controlled pore structure that allows nutrients from the culture medium to reach the deposited cell population, but prevent cultured cells from migrating through the pores. In vitro cell attachment and cell viability can be assessed using scanning electron microscopy, histology, and quantitative assessment with radioisotopes.

The polymeric matrix can be shaped into any number of desirable configurations to satisfy any number of overall system, geometry, or space restrictions. The polymeric matrix can be shaped to different sizes to conform to the organs of different sized patients.

The tissue-engineered construct can be flat, tubular, or of complex geometry. The shape of the construct will be decided by its intended use. The construct can be implanted to repair, supplement, or replace diseased or damaged parts of organs.

In one embodiment, the scaffold material is a hydrogel composed of crosslinked polymer networks that are typically insoluble or poorly soluble in water, but can swell to an equilibrium size in the presence of excess water. For example, the cells can be placed in a hydrogel and the hydrogel injected into desired locations within the organ. In one embodiment, the cells can be injected with collagen alone. In another embodiment, the cells can be injected with collagen and other hydrogels. The hydrogel compositions can include, without limitation, for example, poly(esters), poly(hydroxy acids), poly(lactones), poly(amides), poly(ester-amides), poly (amino acids), poly(anhydrides), poly(ortho-esters), poly (carbonates), poly(phosphazines), poly(thioesters), polysaccharides and mixtures thereof. Furthermore, the compositions can also include, for example, a poly(hydroxy) acid including poly(alpha-hydroxy) acids and poly(betahydroxy) acids. Such poly(hydroxy) acids include, for example, polylactic acid, polyglycolic acid, polycaproic acid, polybutyric acid, polyvaleric acid, and copolymers and mixtures thereof. Due to the unique properties of hydrogels and their potential applications in such areas as controlled drug delivery, various types of hydrogels have been synthesized and characterized. The matrix materials of present invention encompass both conventional foam or sponge materials and the so-called "hydrogel sponges." See, for example, U.S. Pat. No. 5,451,613.

In another embodiment, the scaffold is created using parts of a natural decellularized organ. Parts of organs can be decellularized by removing the entire cellular and tissue content from the organ. See, for example, U.S. Pat. No. 6,479,064.

The expanded cells of the invention can be used for gene therapy in patients in need thereof. In some embodiments, more mature lineage committed cells will be useful, especially where transient gene expression is needed or where gene transduction is facilitated by the maturation and division of the cells. For example, some retroviral vectors require that the cell be cycling for the gene to be integrated. Methods for transducing stem and progenitor cells to deliver new and therapeutic genes are known in the art. See, for example, Smith (1992) Hematother. 1:155. Congenital diseases, which can be treated by gene therapy, include, but are not limited to, introducing new functional genes such as those to treat beta-thalassemia, sickle cell anemia, recombinase deficiency, and adenosine deaminase deficiency. In infectious disease and in cancer, the expanded cells of the invention can be transduced with genes that confer specific resistance to a pathogen or a chemotherapeutic agent, thereby ensuring long-term survival of the transduced cells in vivo.

In another embodiment, differentiated cells may be derived from SPCs in culture. In transfusion medicine, there is a need for alternative blood cell sources, dictated by shortages due to limited blood donations as well as the risk of infectious disease transmission. Expansion of hematopoietic SPCs with concurrent differentiation in the media disclosed herein may be used to grow blood cells for transfusion in vitro. In particular, G2 media may be used to grow red blood cells.

The following examples are offered by way of illustration and not by way of limitation.

EXPERIMENTAL

For these examples, cytokines were used in a non-limiting manner in the defined cytokine media G2, F2, D6, F2N, F4, and G8 described above in concentrations as described in Table 1.

TABLE 1

Cytokine Concentrations in Experimental Media

| Cytokine Abbreviation | Cytokine Full Name | Vendor | Concentration (ng/ml) |
|---|---|---|---|
| Angiotensin | Angiotensin I, II, and III mixture | Sigma, MO | 500 |
| BMP-4 | Bone Morphogenic Protein 4 | R&D Systems, MN | 0.5 |
| BDNF | Brain-Derived Neurotrophic Factor | R&D Systems, MN | 1 |
| PD-ECGF | Platelet-Derived Endothelial Cell Growth Factor | R&D Systems, MN | 2 |
| EGF | Epidermal Growth Factor | BD Biosciences, NC | 0.1 |
| EPO | EPO | R&D Systems, MN | 3 units/ml |
| bFGF | Basic Fibroblast Growth Factor | R&D Systems, MN | 2.5 |
| Fibronectin | Fibronectin | BD Biosciences, NC | 10 |
| Flt-3/Flk-2 ligand | Flt-3/Flk-2 ligand | R&D Systems, MN | 5 |
| G-CSF | Granulocyte Colony Stimulating Factor | R&D Systems, MN | 1 |
| GM-CSF | Granulocyte-Macrophage Colony Stimulating Factor | BD Biosciences, NC | 1 |
| VTCG (SEQ ID NO: 1) | Hematopoietic Adhesion Peptide | Bachem Bioscience, PA | 500 |
| IGF-1 | Insulin-like Growth Factor 1 | R&D Systems, MN | 2.5 |
| IL-11 | Interleukin-11 | R&D Systems, MN | 0.1 |
| IL-3 | Interleukin-3 | R&D Systems, MN | 1 |
| IL-5 | Interleukin-5 | R&D Systems, MN | 0.1 |
| IL-6 | Interleukin-6 | R&D Systems, MN | 0.2 |
| LIF | Leukocyte Inhibitory Factor | Chemicon | 50 |
| M-CSF | Macrophage Colony Stimulating Factor | R&D Systems, MN | 0.5 |
| MCP-1 | Monocyte Chemotactic Protein-1/CCL2 | R&D Systems, MN | 5 |

TABLE 1-continued

Cytokine Concentrations in Experimental Media

| Cytokine Abbreviation | Cytokine Full Name | Vendor | Concentration (ng/ml) |
|---|---|---|---|
| PDGF-AB | Platelet-Derived Growth Factor, containing both the A chain and B-chain heterodimer | R&D Systems, MN | 1 |
| PlGF | Placenta Growth Factor | R&D Systems, MN | 1 |
| TRANCE | TNF-related activation induced cytokine | R&D Systems, MN | 5 |
| SCF | Stem Cell Factor | R&D Systems, MN | 2 |
| SCGF-α | Stem Cell Growth Factor α | Peprotech | 2.5 |
| SDF-1alpha | Stromal Cell-Derived Factor 1 alpha | R&D Systems, MN | 3 |
| TGF-beta1 | Transforming Growth Factor beta 1 | R&D Systems, MN | 0.5 |
| TPO | Thrombopoietin | R&D Systems, MN | 1 |
| VEGF | Endocrine gland-derived vascular endothelial growth factor | R&D Systems, MN | 2.5 |
| Thrombospondin | Thrombospondin | Sigma, MO | 10 |

Example 1

Identification of Culture Media

Media compositions that support the expansion of cord blood-derived CD34+ cells were identified. Screening plates were prepared using 96-well plates containing 30 factors in 60 different compositions. One thousand cord blood-derived CD34+ cells were incubated in each well for 7 days. Each experiment contained 3 repeats and each screen was repeated two more times so that 3 different cord blood preparations were tested in total. Following the 7 day incubation period, the cultured cells were characterized by 4-color flow cytometry (FACS, BD Biosciences, NC). The expanded cells were stained using a combination of 7AAD (to select dead cells), CD34 (to select stem/progenitor cells), CD33 (to select myeloid cells) and CD38 (to select maturing hematopoietic cells). Best media compositions were selected based on the average number of live cells and CD34+ cells obtained from the repeats from each screen.

Factor concentrations were selected based on literature values or reported $ED_{50}$ values for each factor. A commercially available basic cell culture medium (Stemline, Sigma) was chosen that is known to support hematopoietic stem and progenitor expansion when growth factors and cytokines are added.

Best well "hits" of the cytokine screen were the G2, F2, and D6 wells, respectively.

The G2 well contained cytokines fibronectin, SDF-1α, IL-6, SCF, IL-5, BDNF, PD-ECGF, IL-11, IL-3, EPO, Flt-3/Flk-2 ligand, BMP-4, thrombospondin, IGF-1, and bFGF.

The F2 well contained cytokines angiotensin, IL-6, SCF, BDNF, IL-3, PDGF-AB, BMP-4, TGF-β1, thrombospondin, GM-CSF, VEGF, EGF, bFGF, M-CSF, and MCP-1.

The D6 well contained cytokines PlGF, SDF-1α, IL-6, SCF, IL-5, BDNF, IL-11, IL-3, EPO, PDGF-AB, Flt-3/Flk-2 ligand, hematopoietic adhesion peptide comprising the amino acid sequence VTCG (SEQ ID NO:1), TRANCE, GM-CSF, VEGF, and G-CSF.

Cytokine compositions of wells G2, F2, and D6 are referred to hereinafter as "G2," "F2," and "D6," respectively. Following thorough characterization of the expanded cells, including, for example, phenotyping, gene array studies and in vivo animal engraftment studies, the G2 combination was used to support expansion of functional cord blood cells that can successfully engraft sub-lethally irradiated NOD/SCID mice, as described below.

The G2 medium, by way of example, contained 15 factors representing a highly complex mixture. A second level screen, based on results obtained with G2 as described above, was carried out to ascertain whether other combinations of factors would also support expansion.

The second level screen was designed using a Plackett-Burman design with 21 factors, resulting again in 60 unique complex combinations that were created in a basic cell culture media (Stemline, Sigma) in the inner 60 wells of a 96-well plate.

One thousand cord blood derived CD34+ cells were incubated in each well. Three repeats were created and the screen was repeated two more times to cover three different cord blood preparations. The best well "hit" from the first level screen, G2, was used as a control and "hits" were defined as conditions that resulted in more live cells and CD34+ cells after 7-Day incubation as compared to G2.

Following the 7-Day incubation period, the cultured cells were characterized by 4-color flow cytometry (FACS, BD Biosciences, NC). The expanded cells were stained using a combination of 7AAD (to select dead cells), CD34 (to select stem/progenitor cells), CD33 (to select myeloid cells) and CD38 (to select maturing hematopoietic cells). The best media compositions were selected based on the average number of live cells and CD34+ cells obtained from the repeats from each screen.

Although there was significant variation in response between the three cord blood preparations, the best well "hits" were consistently F2N, F4, and G8 wells.

The F2N well contained cytokines BDNF, bFGF, EPO, fibronectin, Flt-3/Flk-2 ligand, IGF-1, IL-11, IL-3, IL-5, SCF, TGF-β1, G-CSF, and GM-CSF.

The F4 well contained cytokines bFGF, EPO, Flt-3/Flk-2 ligand, IL-11, IL-6, PD-ECGF, thrombospondin, and Tpo.

The G8 well contained cytokines BDNF, bFGF, Flt-3/Flk-2 ligand, IL-3, IL-6, PD-ECGF, SCF, G-CSF, LIF, and SCGF-α.

All of these hits except for F4 had more live cells following 7 day expansion than the previous "best well" media G2 from the first-level screen. Surprisingly, although expansion in well F4 was significantly less than the other conditions, the cell composition in well F4 comprised approximately 50% CD34$^{br}$ cells (see Example 2). Cytokine compositions of wells F2N, F4, and G8 are referred to hereinafter as "F2N," "F 4," and "G8," respectively.

This example illustrates that complex mixtures of growth factors could be identified that lead to the expansion of primary mammalian cells of therapeutic value. The number of growth factors needed can be reduced while maintaining or even boosting cell expansion. An optional third-level screen of the above factors may be used to reduce the number of growth factors needed even further or may be used to optimize the concentration of each component of the media. In addition, as shown below, the observed expansion was achieved while maintaining functional characteristics of these cells such as their capacity for engraftment in an animal model.

Example 2

Expanding Umbilical Cord Blood HSCs Ex Vivo

Media (G2, F2, and D6)

Cell Preparation

A 6% hetastarch solution was added to cord blood and incubated for 45-60 minutes. During this incubation stage, hetastarch is preferentially taken up by red blood cells. As a consequence, the red cells sink to the bottom of the conical tube and the blood separates into a light plasma/buffy coat fraction on top of the tube and a dark red fraction containing red cells at the bottom of the tube. White blood cells are contained in the plasma as well as in the buffy coat. A 5 ml pipette was slowly dipped into the clear layer, halfway above the buffy coat. The clear layer was then slowly stirred, causing the buffy coat and any cells contained in that layer to move off the red cell layer and into the plasma. The clear layer (plasma and buffy coat mixture) was then collected, centrifuged at 309 g for 5 min, and the supernatant removed and discarded. ACK lysis buffer was then added to the cell pellet and incubated for 10 minutes at room temperature to lyse any remaining red cells. Following the 10 minute incubation, phosphate buffered saline (PBS) containing 2% fetal calf serum (FCS) was added to the cell suspension and the suspension centrifuged again at 309 g for 5 minutes. The supernatant above the cell pellet was removed and discarded.

A count of total viable nucleated cells was obtained by adding a known amount of medium to the white blood cell pellet, removing a small volume of the resulting cell suspension, diluting this portion with trypan blue at a known ratio and counting cells from this suspension in a hemocytometer (dead cells appear blue in this assay). The number of viable cells contained in the original suspension was calculated based on the dilutions used to make the trypan blue-containing sample.

$CD34^+$ Cell Enrichment $CD34^+$ cells were enriched from the nucleated cell fraction of cord blood using magnetic bead technology (AutoMACS™, Miltenyi Biotec, CA). Nucleated cells prepared according to the procedure described above were re-suspended in PBS containing 2% FCS and 2 mM EDTA. Two isolation methods, a direct and an indirect method, were used to isolate $CD34^+$ cells. For the indirect method, a Fc receptor blocking reagent was added and mixed well with the cell suspension. A CD34 hapten-antibody (Miltenyi Biotec, CA) was added, mixed well and incubated for 15 minutes at 6-12° C. Cells were then washed with PBS containing 2% FCS/2 mM EDTA. Cells were resuspended in PBS containing 2% FCS/2 mM EDTA, and anti-hapten microbeads were added. The cell/microbead suspension was mixed well and incubated for 15 minutes at 6-12° C. Cells were washed with PBS containing 2% FCS/2 mM EDTA and filtered through a 70 µM filter. For the direct method, a FcR blocking reagent and CD34 microbeads were added to the suspension, mixed well and incubated for 30 minutes at 6-12° C. Cells were then washed with PBS containing 2% FCS/2 mM EDTA and filtered through a 70 µM filter. Following filtration for both the indirect and direct method, cell suspensions were then separated on an AutoMACS™ (Miltenyi Biotec, CA) and purity of the resulting $CD34^+$ cell fraction was determined using flow cytometry.

Media Preparation

Cells were maintained in Stemline™ Medium (Sigma, St Louis, Mo., S-0189) supplemented with 1% Penicillin/Streptomycin and 4 mM Glutamine. Growth factors were thawed and added directly into the media at the appropriate concentrations. Medium and components were prepared fresh on the day of study.

Cell Culture 1) 96-well plates: 1,000 $CD34^+$ enriched cells were added in 100 µl of medium, e.g., G2, F2, or D6 medium, and incubated at 37° C. in 5% $CO_2$ for the length of the study.

2) 48-well plates: 2,500 $CD34^+$ enriched cells were added in 1 ml of medium, e.g., G2, F2, or D6 medium, and incubated at 37° C. in 5% $CO_2$ for the length of the study.

3) T-25 flasks: 500,000 cells were added in 10 ml of medium, e.g., G2, F2, or D6 medium, and incubated at 37° C. in 5% $CO_2$ for the length of the study.

Flow Cytometry Analysis

Cells for flow cytometry studies (freshly enriched $CD34^+$ cells or cells expanded in G2, F2, or D6 medium) were suspended in PBS containing 2% FCS. Mouse Fc Block™ was added and incubated at 4° C. for 5 minutes. 1/10 diluted fluorescently labeled antibody mixtures were added and incubated with cell suspensions at 4° C. for 15 minutes. To determine purity of freshly enriched $CD34^+$ cells or cell immunophenotype following expansion in G2, F2, or D6 medium, a mixture of CD34-PE, CD33-FITC, and CD38-APC antibodies were added (BD Pharmingen, CA). For complete immunophenotyping after expansion, a single fluorescently labeled antibody was added to a cell suspension.

Following incubation with the antibody, cells were washed with PBS containing 2% FCS. Cells were then re-suspended in PBS containing 2% FCS and 7-amino actinomycin D to a final concentration of 0.25 µg/ml for detecting dead cells (7-AAD; ViaProbe; BD Biosciences, NC). FACS (BD Biosciences, NC) was used to analyze the cells. At least 10,000 events were collected per cell sample. Flow cytometry data was analyzed using CellQuest software.

Colony-Forming Units Assay

Culture in a growth-factor-containing semisolid medium (MethCult GF H4434™, StemCell Technologies, Vancouver, Calif.) was used to assess the clonogenic potential of freshly isolated cells and cells expanded in G2, F2, or D6 medium for up to 14 days. This particular semisolid medium contained SCF, IL-3, GM-CSF, and EPO. Cells were suspended in Stemline™ medium (Sigma) and then added to MethCult GF H4434™. Cells in semisolid medium were cultured in 35 mm culture dishes, each placed into 150 mm petri dishes containing an open sterile water-containing 35 mm petri dish to minimize evaporation from the semisolid culture. The 150 mm petri dishes containing the 35 mm dishes were kept in a 37° C. incubator with an atmosphere of 5% $CO_2$ and at least 95% humidity. Colonies were scored following 14-16 days of incubation according to manufacturer's recommendations.

Results

Expansion Yield

Cell numbers increased as a function of time during culture in G2, F2, and D6 media. For example, when cultured in 48-well plates, after 19 days of culture, the highest increase, 408-fold was seen for D6 medium, the second highest for G2 medium, 208-fold, followed by F2 medium with 188-fold increase in number of total live cells.

The fold increase in cell number was found to strongly depend on the cell concentration in the medium. A lower cell number per ml of medium was found to result in a higher fold increase in cell number. Increasing surface area also positively impacts the expansion yield. Table 2 shows the effect of these culture conditions upon the growth of cells.

TABLE 2

Influence of Cell Densities and Surface Area on CD34+ Enriched Cord Blood
Cell Culture Yield in G2, F2, and D6 Media
Different Culture Conditions Affect The Outcome Results

| | G2 Media | Cell Concentration | Cell Density | Volume | Surface Area | TNC at Day 7 | TNC Fold Increase |
|---|---|---|---|---|---|---|---|
| UCB-29 | T-25 Flask | 50,000/ml | 20000/cm2 | 10 ml | 25 cm2 | 8,500,000 | 17 |
| UCB-29 | 48 Well Plate | 2,500/ml | 3333/cm2 | 1 ml | 0.75 cm2 | 143,300 | 57.32 |
| UCB-15 | 96 Well Plate | 10,000/ml | 3125/cm2 | 0.1 ml | 0.32 cm2 | 9075 | 9.1 |
| | F2 Media | Cell Concentration | Cell Density | Volume | Surface Area | TNC at Day 7 | TNC Fold Increase |
| UCB-29 | T-25 Flask | 50,000/ml | 20000/cm2 | 10 ml | 25 | 10,250,000 | 20.5 |
| UCB-29 | 48 Well Plate | 2,500/ml | 3333/cm2 | 1 ml | 0.75 | 130,000 | 52 |
| UCB-15 | 96 Well Plate | 10,000/ml | 3125/cm2 | 0.1 ml | 0.32 | 8791 | 8.8 |
| | D6 Media | Cell Concentration | Cell Density | Volume | Surface Area | TNC at Day 7 | TNC Fold Increase |
| UCB-29 | T-25 Flask | 50,000/ml | 20000/cm2 | 10 ml | 25 | 11,000,000 | 22 |
| UCB-29 | 48 Well Plate | 2,500/ml | 3333/cm2 | 1 ml | 0.75 | 147,500 | 59 |
| UCB-15 | 96 Well Plate | 10,000/ml | 3125/cm2 | 0.1 ml | 0.32 | 7503 | 7.5 |

Phenotype of Expanded Cells

A flow cytometer (FACS; BD Biosciences, NC) was used to characterize the cell phenotypes contained in the expanded cord blood cell population. For this, CD34+ cells were isolated as described above, placed in cultures with G2, F2, or D6 medium, and were cultured for 7 days as described above. The expanded cell population was distributed in different tubes each containing a different antibody and labeled with said antibodies as described above. The antibodies used for immunophenotyping of CD34+ enriched cells in this study are listed in Table 3 below, and the results of the flow cytometry analysis for immunophenotyping the cells are listed in Table 4.

TABLE 3

Antibodies for Immunophenotyping of CD34+ Enriched Cells

| Antibody to | Characteristic for |
|---|---|
| CD3 (BD Pharmingen, CA) | T-Cells |
| CD14 (BD Pharmingen, CA) | Monocytes |
| CD16 (BD Pharmingen, CA) | Granulocytes, NK lymphocytes, macrophages |
| CD19 (BD Pharmingen, CA) | B-cells |
| CD31 (BD Pharmingen, CA) | Endothelial cells, platelets, leukocytes and their precursors |
| CD33 (BD Pharmingen, CA) | Myeloid progenitor cells |
| CD34 (BD Pharmingen, CA) | Hematopoietic stem and progenitor cells |
| CD38 (BD Pharmingen, CA) | Differentiating hematopoietic cells |
| CD42a (BD Pharmingen, CA) | Platelets, Megakaryocytes |
| CD71 (BD Pharmingen, CA) | Expressed, typically at high levels, on all proliferating cells, erythroid precursors |
| CD133 (Miltenyi Biotec, CA) | Hematopoietic and $CD34^{br}$ stem and progenitor cells, neural stem cells |

TABLE 4

Immunophenotyping of CD34+ Enriched Cells Cultured in G2, F2, or D6 Medium for Seven Days

| | T0 CD34+ Cells (%) | | Day 7 G2 Medium (%) | | | Day 7 F2 medium (%) | | Day 7D6 medium (%) | |
|---|---|---|---|---|---|---|---|---|---|
| | UCB-30 p37 03-8283-43 | UCB-31 p44 03-8283-43 | UCB-14 p70 03-8283-23 | UCB-21 p4 03-8283-43 | UCB-29 p42 03-8283-43 | UCB-21 p4 03-8283-43 | UCB-29 p42 03-8283-43 | UCB-21 p4 03-8283-43 | UCB-29 p42 03-8283-43 |
| CD3 | 0 | 12 | 0 | 0 | 0 | 0 | 0.1 | 0 | 0 |
| CD14 | 2 | 1 | 9 | 6.88 | 7 | 5 | 11 | 5 | 7 |
| CD16 | 5 | 9 | 0 | 0 | 0.15 | 0 | 0.1 | 0 | 0.5 |
| CD19 | 4 | 4 | 0 | 0 | 0 | 0 | 0 | 0 | 0 |
| CD31 | 89 | 98 | ND | ND | 89 | ND | 58 | ND | 83 |
| CD33 | 70 | 86 | 89 | 65 | 76 | 57 | 66 | 68 | 86 |
| CD34 | 81 | 96 | 37 | 46 | 28 | 28 | 19 | 28 | 22 |
| CD38 | 15 | 31 | 0 | 1 | 4 | 1 | 3 | 0.28 | 4 |
| CD42a | 7 | 8 | 4 | 1 | 5 | 6 | 5 | 3 | 4 |
| CD71 | 24 | 55 | 72 | 75 | 43 | 42 | 48 | 57 | 56 |
| CD133 | 53 | 81 | 19 | 31 | 19 | 6 | 5 | 14 | 15 |

Few T-cells (CD3), B-cells (CD19) or mature granulocytes, NK lymphocytes, or macrophages (CD16) were found after expansion in either F2, G2, or D6 media. A small number of monocytes (CD14) and platelets or megakaryocytes (CD42a) were found in the expanded cell population. A high number of cells were found to express surface markers characteristic of endothelial cells, platelets, leukocytes or their precursors (CD31), of myeloid progenitor cells (CD33), of hematopoietic stem and progenitor cells (CD34), of proliferating cells and erythroid precursors (CD71), and of hematopoietic and CD34$^+$ stem and progenitor cells or neural stem cells (CD133). Surprisingly, the expression of CD38, a marker typically expressed on differentiating hematopoietic cells, almost disappeared after 7 days of culture in all three media.

Another surprising finding was the expanded CD34 expression pattern following expansion in G2, F2, and D6 media. A distinct CD34$^{br}$ population was present after expansion for 7 days in G2 medium, with significantly more cells expressing CD34 at this higher level as compared to the ingoing CD34$^+$ cell population. This was also observed, although to a lesser extent, with F2 and D6 media.

Additional immunophenotyping studies were conducted following expansion of cells in G2 medium using cell culture and flow cytometry methods as described above. Fold expansion for total nucleated cells (TNCs) and CD34 expression results following 7 day culture are summarized in Table 5. Table 6 shows the percentage of these expanded cells expressing various cell receptor/markers in CD34$^{br}$ cells (as replicated in three experimental runs). Table 7 shows the percentage of these expanded cells expressing various cell receptor markers in CD34$^{dim}$ cells (as replicated in three experimental runs).

TABLE 5

Fold Expansion and CD34 Expression Results Following Expansion in G2 Medium

|  | TNC Fold Increase | CD34$^+$ Fold Increase | % CD34$^+$ | % CD34$^{br}$ | % CD34$^{dim}$ |
|---|---|---|---|---|---|
| Average | 11.2 | 3.5 | 34.2 | 19.0 | 12.7 |
| Min | 8.9 | 2.1 | 23.3 | 13.4 | 11.8 |
| Max | 16.9 | 5.4 | 42.6 | 22.2 | 13.4 |

TABLE 6

Cell Receptor/Marker Expression in CD34$^{br}$ Cells Following Expansion in G2 Medium

|  | Expression Markers | Experiment 1 | Experiment 2 | Experiment 3 |
|---|---|---|---|---|
| Adhesion/Homing Markers | CD44 | 97.3 | 99.6 | 98.9 |
|  | CD29 | 98.7 | 99.7 | 98.75 |
|  | CD54 | 94 | 97 | 85.7 |
|  | CD105 | 96.1 | 99.4 | 96.5 |
|  | CD166 | 96.1 | 98.2 | 92.5 |
| Stem/Progenitor Markers | CD133 | 79.2 | 85.2 | 91.9 |
|  | CD117 | 91.3 | 97.7 | 91.4 |
|  | CD90 | 9.36 | 11.7 | 6.84 |
| Endothelial Cell Markers | CD109 | 9.5 | 12.4 | 24.9 |
|  | CD31 | 82.8 | 99.8 | 97.1 |
| Myeloid Markers | CD111 | 13.2 | 9.89 | 14.2 |
| B Cell | CD81 | 92.5 | 97.8 | 86.2 |
| MHC-class II | HLA-DR | 89.7 | 89.8 | 89.8 |

TABLE 7

Cell Receptor/Marker Expression in CD34$^{dim}$ Cells Following Expansion in G2 Medium

|  | Expression Markers | Experiment 1 | Experiment 2 | Experiment 3 |
|---|---|---|---|---|
| Adhesion/Homing Markers | CD44 | 84.7 | 94.5 | 90.7 |
|  | CD29 | 97.6 | 99.2 | 97.5 |
|  | CD54 | 87.4 | 90.4 | 70.9 |
|  | CD105 | 91.1 | 96.3 | 88.9 |
|  | CD166 | 84.7 | 89.8 | 83.1 |
| Stem/Progenitor Markers | CD133 | 36.5 | 43.9 | 51 |
|  | CD117 | 53.9 | 71.3 | 60 |
|  | CD90 | 5.4 | 1.2 | 1.3 |
| Endothelial Cell Markers | CD109 | 50.7 | 47.1 | 54.3 |
|  | CD31 | 44.1 | 96 | 72.5 |
| Myeloid Markers | CD111 | 35.4 | 32.2 | 35.8 |
| B Cell | CD81 | 91.5 | 88.4 | 65.1 |
| MHC-class II | HLA-DR | 79.4 | 84 | 71 |

Expansion of CD34$^+$ and CD34$^{br}$ Cells

Growth curve studies were performed to determine the expansion of CD34$^+$ and CD34$^{br}$ cells in G2, F2, and D6 media. CD34$^+$ enriched cells were prepared as described above. Cells were cultured in G2, F2, or D6 medium in 48-well plates as described above. CD34 expression was determined by flow cytometry as described above at day 0, 4, 7, 11, 14, and 19. Table 8 shows the expansion of CD34$^+$ and CD34$^{br}$ cells respectively in G2, F2, and D6 media. In G2 medium, up to a 28-fold increase in CD34$^+$ cells on day 7 and up to a 269-fold increase in CD34$^{br}$ cells on day 14 were observed.

TABLE 8

Growth Curve Study Data - Expansion of CD34$^+$ and CD34$^{br}$ Cells in G2, F2, and D6 Media

| G2 media | Day zero | Day 4 | Day 7 | Day 11* | Day 14* | Day 19* |
|---|---|---|---|---|---|---|
| TNC | 2500 | 18889 | 143300 | 390000 | 565000 | 520000 |
| TNC Fold Increase |  | 7.56 | 57.32 | 156 | 226 | 208 |
| CD34% | 82.39% | ND | 41.49% | 4.90% | 9.17% | 9.31% |
| CD34br % | 3.63% | ND | 11.59% | 0.10% | 4.34% | 2.73% |
| CD34 | 2060 | ND | 58753 | 19110 | 51811 | 48412 |
| CD34br | 91 | ND | 16608 | 390 | 24521 | 14196 |
| CD34 Fold Increase |  | ND | 28.5 | 9.3 | 25.2 | 23.5 |
| CD34br Fold Increase |  | ND | 183 | 4.3 | 269 | 156 |

TABLE 8-continued

Growth Curve Study Data - Expansion of CD34$^+$ and CD34$^{br}$ Cells in G2, F2, and D6 Media

| F2 media | Day zero | Day 4 | Day 7 | Day 11 | Day 14 | Day 19 |
|---|---|---|---|---|---|---|
| TNC | 2500 | 12778 | 130000 | 276250 | 415000 | 470000 |
| TNC Fold Increase | | 5.11 | 52 | 110.5 | 166 | 188 |
| CD34% | 82.39% | ND | 35.20% | 1.13% | 2.98% | 1.30% |
| CD34br % | 3.63% | ND | 8.61% | 0.03% | 0.71% | 0.17% |
| CD34 | 2060 | ND | 45500 | 3122 | 12367 | 6110 |
| CD34br | 91 | ND | 11193 | 83 | 2947 | 799 |
| CD34 Fold Increase | | ND | 22.1 | 1.5 | 6 | 3 |
| CD34br Fold Increase | | ND | 123 | 0.9 | 32.4 | 8.8 |

| D6 media | Day zero | Day 4 | Day 7 | Day 11 | Day 14 | Day 19 |
|---|---|---|---|---|---|---|
| TNC | 2500 | 21111 | 147500 | 403750 | 720000 | 1020000 |
| TNC Fold Increase | | 8.4 | 59 | 161.5 | 288 | 408 |
| CD34% | 82.39% | ND | 25.64% | 2.87% | 4.85% | 3.06% |
| CD34br % | 3.63% | ND | 6.16% | 0.14% | 2.14% | 0.86% |
| CD34 | 2060 | ND | 36875 | 11588 | 34920 | 31212 |
| CD34br | 91 | ND | 9086 | 565 | 15408 | 8772 |
| CD34 Fold Increase | | ND | 17.9 | 5.6 | 17 | 15.2 |
| CD34br Fold Increase | | ND | 99.8 | 6.2 | 169 | 96.4 |

*Semi-depletion feeding

In D6 media, extensive expansion was observed, and by day 19 the culture started turning pink, indicating the presence of hemoglobin and demonstrating that some cells had differentiated into erythrocytes.

Function of Expanded Cells—In Vitro Colony Forming Units

The function of the expanded cells was explored by their ability to form colonies in colony forming assays. The assays were performed as described above. Colony-forming units increased up to 36-fold (D6 medium, day 11). Cells maintained in these three cytokine cocktail media cultured up to 11 days still had clonogenic potential, indicating that immature progenitor cells are maintained in these cultures.

Microscopy analysis of colonies formed in this assay was performed to determine the phenotype of colony-forming cells in the expanded cell population. Cells expanded in D6 medium formed mostly BFU-E/CFU-E, (burst-forming unit-erythroid/colony forming unit erythroid, e.g., colonies characteristic for erythroid progenitor cells; data not shown). Cells expanded in G2 and F2 formed mainly a mixture of BFU-E/CFU-E and CFU-GM (colony forming units-granulocyte/macrophage, e.g., neutrophil/monocyte progenitors), and also some CFU-GEMM (colony-forming unit-granulocyte, -erythrocyte, -macrophage, and -megakaryocyte, e.g., characteristic for more immature myeloid stem cells)(data not shown).

Table 9 shows the data from the colony forming unit assay for CD34$^+$ enriched cord blood cells expanded in G2, F2, and D6 media.

TABLE 9

Data from Colony Forming Unit Assays for CD34$^+$ Enriched Cord Blood Cells Expanded in G2, F2, or D6 Medium.

| | Day zero | Day 4 | Day 7 | Day 11* |
|---|---|---|---|---|
| G2 media | | | | |
| TNC | 2500 | 18889 | 143300 | 390000 |
| TNC Fold Increase | | 7.56 | 57.32 | 156 |
| CFU plate efficiency | 16.45% | 9.10% | 6.69% | 1.60% |

TABLE 9-continued

Data from Colony Forming Unit Assays for CD34$^+$ Enriched Cord Blood Cells Expanded in G2, F2, or D6 Medium.

| | Day zero | Day 4 | Day 7 | Day 11* |
|---|---|---|---|---|
| CFU | 411.25 | 1719 | 9587 | 6240 |
| CFU Fold Increase | | 4.18 | 23.3 | 15.2 |
| F2 media | | | | |
| TNC | 2500 | 12778 | 130000 | 276250 |
| TNC Fold Increase | | 5.11 | 52 | 110.5 |
| CFU plate efficiency | 16.45% | 8.78% | 6.75% | 1.05% |
| CFU | 411.25 | 1122 | 8775 | 2901 |
| CFU Fold Increase | | 2.73 | 21.3 | 7.1 |
| D6 media | | | | |
| TNC | 2500 | 21111 | 147500 | 403750 |
| TNC Fold Increase | | 8.4 | 59 | 161.5 |
| CFU plate efficiency | 16.45% | 11.10% | 5.30% | 3.72% |
| CFU** | 411.25 | 2343 | 7818 | 15020 |
| CFU Fold Increase | | 5.7 | 19 | 36.5 |

*Semi-depletion feeding
**most of CFUs are CFU-E

Function of CD34$^+$ and CD34$^{br}$ Cells Following Seven Day Expansion in G2 Medium Plating efficiencies of freshly isolated and enriched CD34$^+$ cells (82.4% purity) of cells expanded in G2 medium for 7 days and of CD34$^{br}$ cells isolated by flow cytometric sorting from a cell population expanded in G2 medium for 7 days were determined experimentally using the colony forming assay described above. The plating efficiencies in this experiment were 16.5%, 7%, and 21.3%, respectively, as show in Table 10 below.

TABLE 10

CFU Plating Efficiency for Ingoing CD34+ Cells in G2 Medium

CFU Plating Efficiency (%)

| Ingoing CD34 cells | CD34 cells cultured in G2 for 7 days | |
|---|---|---|
| TNC | TNC | CD34br |
| 16.5 | 6.7 | 21.3 |

Although the plating efficiencies for 100% pure CD34+ cells before and after expansion were not determined, and determination of the plating efficiency of freshly isolated 100% pure CD34$^{br}$ cells is not practical due to the large amount of cord blood that would be needed because these cells are so rare, it is still possible to give an estimate for these numbers (see Table 10). In these instances, the CFU plating efficiency for ingoing CD34+ cells (80-90% pure ingoing CD34+) and Day 7 TNCs (30-40% pure ingoing CD34+) is from sample UCB-29; the CFU plating efficiency for Day 7 CD34$^{br}$ (approximately 90% pure ingoing CD34+) is from sample UCB-31. The freshly isolated and enriched CD34+ cell population was 82.4% pure, in other words, 82.4 out of 100 cells were CD34+. The plating efficiency for that population was determined to be 16.5%; thus, out of 100 cells from that 82.4% pure CD34+ population, 16.5 cells form colonies. Since 82.4 of 100 cells were CD34+, about 20 CD34+ cells from this cell population form colonies, e.g., the plating efficiency for 100% pure CD34+ cells before expansion is approximately 20%. Table 11 shows the CFU plating efficiency in ingoing CD34+ cells and cells cultured in G2 medium for 7 days. The disclosure of ranges within the table indicates approximate values.

TABLE 11

CFU Plating Efficiency for TNCs and CD34+ and CD34$^{br}$ Cells in G2 Medium

| Ingoing CD34 Cells | | | CD34 Cells Cultured in G2 for 7 Days | | |
|---|---|---|---|---|---|
| TNC | CD34+ | CD34$^{br}$ | TNC | CD34+ | CD34$^{br}$ |
| 16.5 | 20.0 | 20-100 | 6.7 | 6.7-16.1 | 9.1-21.3 |

CD34$^{br}$ cells are a small portion of these CD34+ cells, and it is thus reasonable to assume a plating efficiency for these cells that is close to that of the 100% pure CD34+ cell population before expansion. However, due to the high expression of CD34, it is also reasonable to assume that the most stem-like cells are contained in this population, and thus this population has the greatest colony forming potential. Thus, an upper limit for the plating efficiency of 100% pure CD34$^{br}$ cells before expansion is assumed. However, due to the high expression of CD34, it is also reasonable to assume that the most stem-like cells are contained in this population, and thus this population has the greatest colony-forming potential.

Following expansion, the plating efficiency of the 41.5% CD34+ containing cell population was determined to be 6.7%. This to also estimated be the lower limit for the plating efficiency of 100% pure CD34+ cells isolated from the expanded cell population. As an upper limit for plating efficiency of 100% pure CD34+ cells isolated from the expanded cell population, a similar calculation as described above for the ingoing cell population was performed. Of 100 cells from the expanded cell population, 6.7 cells form colonies and 41.5 of these 100 cells are CD34+ cells. Assuming that all observed colonies originate from CD34+ cells only, a plating efficiency of 16.1% for 100% pure CD34+ cells isolated from the expanded cell population was calculated.

Based on these CFU plating efficiency estimates and the cell numbers shown in Table 12 below, the number of CFUs and the fold increase in CFUs after culture in G2 medium for 7 days was calculated. The disclosure of ranges within the table indicates approximate values. Table 12 shows the number of ingoing CD34+ cells, the number of CD34+ cells after 7 days in G2 medium, and the fold increase. Table 13 shows the number of CFUs for the same categories.

TABLE 12

CD34+ Cell Number and Fold Increase After 7 Days in G2 Medium

Number of Cells

| Ingoing CD34 cells | | | CD34 cells cultured in G2 for 7 days | | | Fold-Increase | | |
|---|---|---|---|---|---|---|---|---|
| TNC | CD34+ | CD34br | TNC | CD34+ | CD34br | TNC | CD34+ | CD34br |
| 2500 | 2060 | 91 | 143300 | 59470 | 16608 | 57.3 | 28.9 | 182.5 |

TABLE 13

CD34+ CFU and Fold Increase After 7 Days in G2 Medium
Number of CFU

| Ingoing CD34 cells | | | CD34 cells cultured in G2 for 7 days | | | Fold-Increase | | |
|---|---|---|---|---|---|---|---|---|
| TNC | CD34+ | CD34br | TNC | CD34+ | CD34br | TNC | CD34+ | CD34br |
| 413 | 412 | 18-91 | 9601 | 3984-9575 | 3538 | 23.2 | 9.7-23.2 | 38.9-196.6 |

FIG. 1 summarizes the results of expansion of CD34+ enriched cells from UCB for 7 days in G2 medium. The figure shows a 57-fold increase in total live cell number, a 29-fold increase in CD34+ cells and a 183-fold increase in CD34$^{br}$ cells; a 23-fold increase in total CFUs, a 10- to 23-fold increase in CD34+ originated CFUs and a 39- to 197-fold increase in CFUs.

Media (F2N, G8, and F4)

Media formulations F2N, G8, and F4 were also tested for their ability to support ex vivo expansion of CD34 cells using cell preparation, cell enrichment, media preparation, cell culture, and flow cytometer analysis methods as described above.

Cell numbers increased as a function of time during culture in G2, G8, F2N, and F4 media over a period of approximately three weeks (22 days). For example, after 22 days of culture, a 45.70 fold increase was seen for the F2 medium, a 37.77 fold increase for the G2 medium, a 24.86 fold increase for the G8 medium, and a 2.21 increase for the F4 medium. Although the F4 medium resulted in significantly less expansion than the other media, it did maintain the preferred stem and progenitor cell phenotype, as described elsewhere herein.

CD34+ enriched cells were cultured in G2, F2N, G8, and F4 media for 7 days, after which CFU assays were conducted as described above. As shown in Table 14, CD34$^{br}$ cells expanded in F2N and F4 media have similar plating efficiency compared to the ingoing cells. In addition, CD34$^{br}$ cells expanded in F2N medium had a higher percentage of BFU-E and lower percentage of CFU-GM compared to CD34$^{br}$ cells expanded in F4 medium. Table 15 shows that expanded TNC in F4 medium gave the highest plating efficiency compared to other three media.

TABLE 14

CFU Plating Efficiency for Expanded CD34$^{br}$ Cells in F2N, G8, and F4 Media

| Cell Type | CFU-M | CFU-GEMM | CFU-GM | BFU/CFU-E | Total CFUs | Average CFUs | Plating Efficiency (%) |
|---|---|---|---|---|---|---|---|
| Fresh | 4 | 12 | 46 | 89 | 167 | 157.5 | 31.5 |
| CD34+ | 8 | 9 | 40 | 75 | 148 | | |
| G02 | 8 | 7 | 29 | 17 | 61 | 67 | 13.4 |
| CD34$^{br}$ | 15 | 4 | 25 | 29 | 73 | | |
| G08 | 19 | 8 | 28 | 24 | 79 | 83 | 16.6 |
| CD34$^{br}$ | 18 | 10 | 40 | 19 | 87 | | |
| F02 | 4 | 6 | 46 | 122 | 178 | 163.5 | 32.7 |
| CD34$^{br}$ | 7 | 10 | 43 | 89 | 149 | | |
| F04 | 7 | 5 | 76 | 35 | 123 | 128.5 | 25.7 |
| CD34$^{br}$ | 14 | 6 | 85 | 29 | 134 | | |

TABLE 15

CFU Plating Efficiency for Expanded TNC Cells in F2N, G8, and F4 Media

| Cell Type | CFU-M | CFU-GEMM | CFU-GM | BFU/CFU-E | Total CFUs | Average CFUs | Plating Efficiency (%) |
|---|---|---|---|---|---|---|---|
| Fresh | 4 | 12 | 46 | 89 | 167 | 157.5 | 31.5 |
| CD34+ | 8 | 9 | 40 | 75 | 148 | | |
| G02 | 8 | 11 | 50 | 75 | 144 | 159.5 | 6.38 |
| TNC | 10 | 11 | 44 | 110 | 175 | | |
| G08 | 7 | 5 | 35 | 77 | 124 | 124 | 4.96 |
| TNC | 9 | 4 | 54 | 57 | 124 | | |
| F02 | 8 | 13 | 32 | 73 | 126 | 120.5 | 4.82 |
| TNC | 10 | 17 | 29 | 59 | 115 | | |
| F04 | 12 | 12 | 126 | 133 | 283 | 250 | 10.0 |
| TNC | 6 | 10 | 93 | 108 | 217 | | |

Example 3

Expansion Yield Under Different Oxygen Tension Conditions

CD34+ enriched cells were prepared and cultured as described in Example 2 using G2 medium. Cell culture was carried out in T-25 flasks (either lying down or inverted) or 48-well plates. Flow cytometry analyses and colony-forming units assays were carried out as describe in Example 2.

Cell Culture

1) T-25 Flasks (Lying Down):
   a) 2,500 cells were added to 10 ml of G2 medium and incubated at 37° C. in 5% or 20% $O_2$ for the length of the study.
   b) 8,300 cells were added to 10 ml of G2 medium and incubated at 37° C. in 5% $O_2$ for the length of the study.
2) T-25 Flasks (Inverted):
   a) 2,500 cells were added to 50 ml of G2 medium and incubated at 37° C. in 5% or 20% $O_2$ for the length of the study.
   b) 2,700 cells were added to 10 ml of G2 medium and incubated at 37° C. in 5% or 20% $O_2$ for the length of the study.
3) 48-Well Plates:
   a) 2,500 cells were added to 1 ml of G2 medium and incubated at 37° C. in 5% or 20% $O_2$ for the length of the study.
   b) 5,000 cells were added to 1 ml of G2 medium and incubated at 37° C. in 5% or 20% $O_2$ for the length of the study.

Results

The fold increase was found to strongly depend on the oxygen tension of the culture condition. In each case, the 5% $O_2$ condition yielded a greater fold increase compared to the 20% $O_2$ condition. Table 16 shows the effect of these culture conditions upon the growth of cells.

TABLE 16

Influence of Oxygen Tension on CD34+ Enriched Cord Blood Cell Culture Yield in G2 Media.

| Culture Vessel | Cells/ml | Media volume | Surface Area (cm2) | Cells/cm2 | Fold Increase 5% O2 | Fold Increase 20% O2 |
|---|---|---|---|---|---|---|
| T-25 Flask Lying Down | 2,500 | 10 | 25 | 1000 | 8.3 | 5.74 (5.1-6.7) |
| T-25 Flask Lying Down | 8,300 | 10 | 25 | 3320 | 16.6 (15.4-16.80) | NA |
| T-25 Flask Inverted | 2,500 | 50 | 8 | 15,625 | 14.2 (12.5-15.9) | 10.6 (10.6-10.7) |
| T-25 Flask Inverted | 2,700 | 10 | 8 | 3373 | 21.9 (18.8-27.7) | 10.6 (4.3-14.2) |
| 48-well plate | 2,500 | 1 | 0.75 | 3333 | 21.1 (18.6-22.5) | 13.7 (9.9-16.9) |
| 48-well plate | 5,000 | 1 | 0.75 | 6666 | 11.5 (8.5-15.4) | 6.2 (5.2-8.0) |

Example 4

Expansion Yield Using Lin− and CD133+ Cell Starting Populations

Lin− Cell Enrichment

Lin− cell enrichment was carried out using G2 and D6 media. Cells were isolated from umbilical cord blood as described in Example 2 and re-suspended at a density of between $2\times10^7$ cells/ml and $8\times10^7$ cells/ml (preferably $5\times10^7$ cells/ml) in PBS plus 2% FCS. StemSep Primitive Progenitor Enrichment Cocktail (StemCell Technologies, Vancouver, Calif.) was added at a concentration of 100 µl per ml of cell solution and mixed well. Cells were incubated on ice for 30 minutes or at room temperature for 15 minutes.

Lin− cells were enriched using magnetic bead technology as described by the manufacturer (StemCell Technologies, Vancouver, Calif.). The column was placed in the magnet and assembled, and primed with PBS according to manufacturer instructions. The column was washed with 25 ml of PBS plus 2% FCS. Magnetic colloid was added at a concentration of 60 µl per ml of cell solution, mixed well and incubated on ice for 30 minutes or at room temperature for 15 minutes. The sample was loaded, followed by a 25 ml wash with PBS plus 2% FCS. The sample was collected and checked for purity by FACS analysis. Cell viability was checked by trypan blue exclusion.

Cells were maintained in G2 and D6 media as described in Example 2. Cell culture methods, flow cytometer analyses, and colony forming unit assays were conducted as described in Example 2.

Results

Both G2 and D6 media supported expansion of Lin− cells, and the resulting cell populations contained CD34+ stem and progenitor cells. Table 17 shows that expansion of Lin− cells in G2 medium resulted in an average 45.7-fold increase of cells with 9.5% of these CD34+ cells, and expansion in D6 media resulted in an average 73.6-fold increase net increase of cells with 7.3% of these CD34+ cells.

TABLE 17

Expansion Yield in G2 and D6 Media Using a Lin− Cell Starting Population.

| Culture Medium | Fold Increase Average | Min/Max | % CD34+ cells | % CD33+ cells | % CD38+ cells |
|---|---|---|---|---|---|
| G2 | 45.7 | 42.1/49.6 | 9.5 | 36.6 | 0.9 |
| D6 | 73.6 | 56/85.8 | 7.3 | 40.0 | 1.9 |

CD133+ Cell Enrichment

CD133+ cells were enriched from the nucleated cell fraction of cord blood using magnetic bead technology (AutoMACS™, Miltenyi Biotec, CA). Nucleated cells prepared according to the procedure described above in Example 2 were resuspended in PBS containing 2% FCS and 2 mM EDTA. An FcR blocking reagent and CD133 microbeads were added to the suspension, mixed well, and incubated for 30 minutes at 6-12° C. Cells were then washed with PBS containing 2% FCS/2 mM EDTA and filtered through a 70 µM filter. Following filtration for both the indirect and direct method, cell suspensions were then separated on an AutoMACS™ (Miltenyi Biotec, CA) and purity of the resulting CD133+ cell fraction was determined using flow cytometry. The purity of enriched CD133+ was 84%, and about 94% of CD133+ cells expressed CD34 antigen.

Cell Culture 48-well plates: 2,500 CD34+ enriched cells were added in 1 ml of medium, e.g., G2, F2, or D6 medium, and incubated at 37° C. in 5% $CO_2$ for the length of the study.

Flow Cytometry Analysis

Cells for flow cytometer studies (freshly enriched CD34+ cells or cells expanded in G2, F2, or D6 medium) were suspended in PBS containing 2% FCS. Mouse Fc Block™ was added and incubated at 4° C. for 5 minutes. Fluorescently labeled antibody mixtures diluted 1:10 were added and incubated with cell suspensions at 4° C. for 15 minutes. To determine purity of freshly enriched CD34+ cells or cell immunophenotyping following expansion in G2, F2, or D6 medium, a mixture of CD34-PE, CD33-FITC, and CD38-APC antibodies were added (BD Pharmingen, CA). The following combinations were also used for this study: CD34FITC/CD133PE, CD34FITC/CD90PE/CD117APC (BD Pharmingen, CA).

Following incubation with the antibody, cells were washed with PBS containing 2% FCS. Cells were then resuspended in PBS containing 2% FCS and 7-amino actinomycin D to a final concentration of 0.25 μg/ml for detecting dead cells (7-AAD; ViaProbe; BD Biosciences, NC). FACS (BD Biosciences, NC) was used to analyze the cells. At least 10,000 events were collected per cell sample. Flow cytometry data was analyzed using CellQuest software.

Results

As shown in Table 18, the CD133+ cells give rise to more total nucleated cells after 7 days expansion in G2, F2, and D6 media compared to CD34+ cells as a starting population (see Table 18).

TABLE 18

Expansion Yield in G2, F2, and D6 Media Using a CD133+ Cell Starting Population.

| Cells | Time Zero G2/F2/D6 | Day 7 G2 | F2 | D6 |
|---|---|---|---|---|
| CD34+ | 91.06% | 28.51% | 21.76% | 20.03% |
| CD34$^{br}$ | ND | 5.83% | 3.4% | 3.32% |
| CD34+/CD33+ | 88.83% | 24.18% | 17.53% | 14.32% |
| CD90+ | ND | 2.61% | 2.04% | 1.21% |
| CD34+/CD90+ | ND | 2.27% | 1.71% | 0.77% |
| CD133+ | 82.58% | 31.26% | 12.2% | 18.51% |
| CD34+/CD133+ | 82.33% | 21.17% | 8.86% | 8.5% |
| CD90+/CD117+ | ND | 1.69% | 1.13% | 0.82% |
| TNC | 2500 cells | 183300 cells | 209200 cells | 319200 cells |
| TNC Fold Increase | | 73.32 fold | 83.68 fold | 127.68 fold |

Example 5

Expansion Yield Using Sequential Expansion Methodology

CD34+ cells were isolated and cultured for 7 days as described in Example 2 using G2 medium. The expanded cells were stained with CD34-PE and sorted by FACS (BD Biosciences, NC) into CD34$^{br}$ and CD34$^{dim}$ cells as described in Example 2. The sorted CD34$^{br}$ and CD34$^{dim}$ cells were then recultured at a density of 2500 cells/ml in G2 medium in a 48 well plate for another 7 days. Cell culture methods and cell analysis, including flow cytometer analyses and colony forming unit assays, were conducted as described in Example 2.

Results

Sequential stages of expansion in G2 medium supported further expansion of CD34$^{br}$, CD34$^{dim}$, and CD34$^-$ cells compared to a single stage of expansion. As shown in Table 19, CD34$^{br}$ cells exhibited a greater expansion potential (average 53.6-fold increase) compared to CD34$^{dim}$ cells (average 27.7-fold increase) and CD34$^-$ cells (average 8.2-fold increase).

TABLE 19

Expansion Yield Using Sequential Expansion in G2 Medium.

| Cell Type | Fold Increase Average | Min/Max |
|---|---|---|
| CD34$^{br}$ | 53.6 | 43.7/68.6 |
| CD34$^{dim}$ | 27.7 | 25.0/30.1 |
| CD34 negative | 8.2 | NA (1 data point only) |

Example 6

In Vivo Function of CD34$^{br}$ Cells in a SCID/NOD Murine Model

Purification of Human Cord Blood CD34+Cells

Three umbilical cord blood (UCB) units were processed according to a procedure published by Rubinstein et al. (1995) Proc. Natl. Acad. Sci. USA, 92:10119-22. Briefly, red blood cells were removed from the UCB by the addition of 6% (wt/vol) hydroxyethyl starch (Sigma) to a final concentration of 1.2%, followed by incubation at room temperature for one hour to obtain a white blood cell-enriched plasma fraction. The plasma fraction was centrifuged for 5 minutes at 1200 rpm, the plasma supernatant was removed and the cell pellet was treated with 20 ml of ammonium chloride lysing buffer for 8 minutes at room temperature. Cells were washed with PBS with 2% FCS and counted. 1×10$^9$ total nucleated cells were obtained in this particular case. This white cell population contained 1.45% CD34+ and 0.55% Thy-1+ cells (as determined by flow cytometry, FACS; BD Biosciences, NC). The white blood cell-enriched pellet was then used for CD34+ cell enrichment using a magnetically activated cell sorter (AutoMACS™, Miltenyi Biotec, CA) according to the manufacturer's instructions. The total nucleated cell count following enrichment was 2.44×10$^6$ cells, and the cell population consisted of 91.13% CD34+ cells (as determined by flow cytometry, FACS; BD Biosciences, NC).

Expansion of Human Cord Blood CD34+Cells

Figure 2:
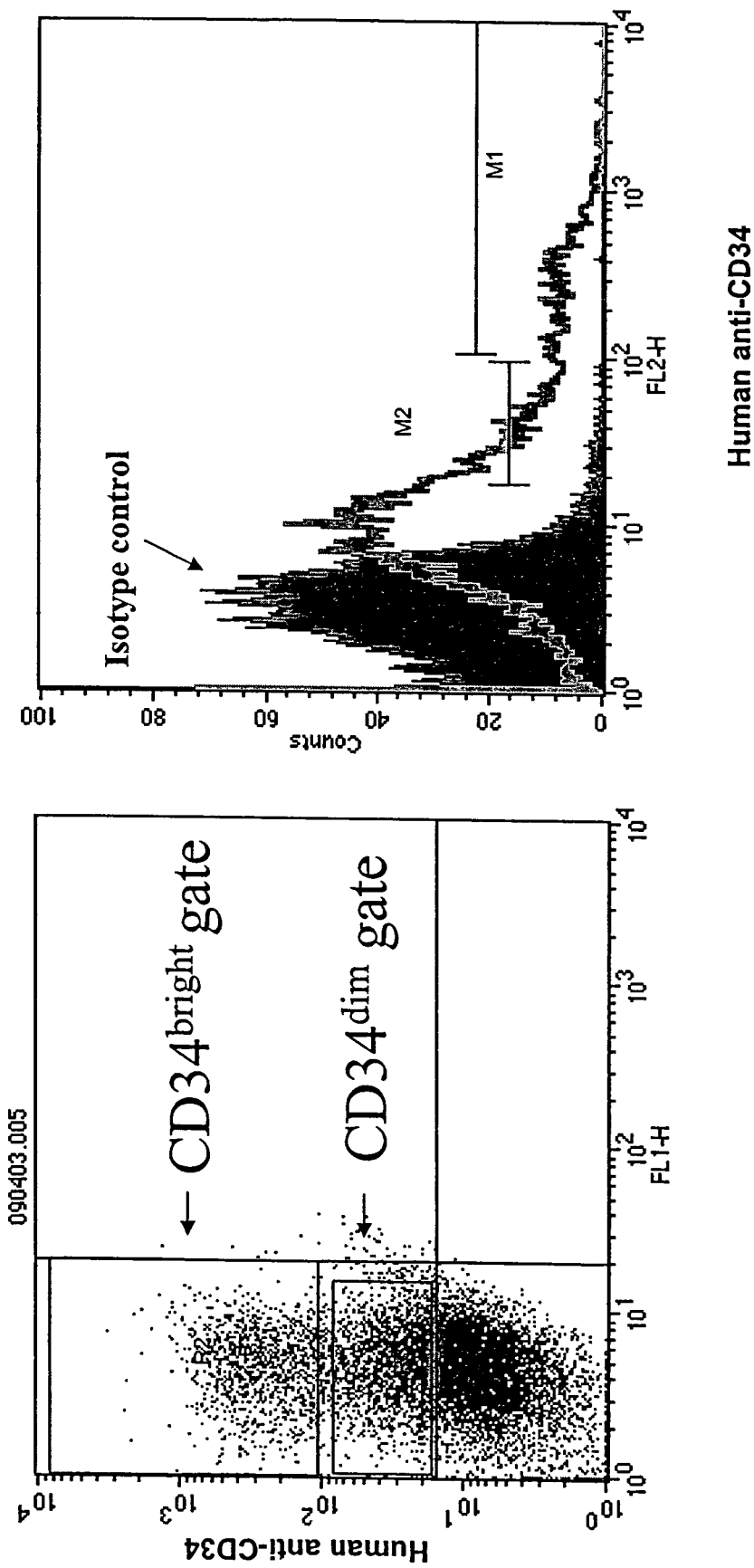
FIG. 2 shows the gating strategy for sorting expanded cells into $CD34^{br}$ and $CD34^{dim}$ cells for NOD/SCID mouse studies.

Enriched CD34+ UCB cells were suspended in Stemline™ medium (Sigma) with G2 cytokine mix and plated at 30,000 cells/well (6 ml/well) into 6-well plates. Cells were cultured for 7 days at 5% CO$_2$ at 99% humidity without any intermediate feedings. Cell viability was determined following culture by trypan blue exclusion and was found to be greater than 95%. Following culture, cells were stained with anti-human-CD34PE (BD Technologies) and sorted using FACS (BD Biosciences, NC) into a CD34$^{br}$ and CD34$^{dim}$ population (see FIG. 2 for gating strategy used to distinguish between these two cell populations). The estimated purity of both cell populations was about 95% following flow cytometer sorting.

Colony-Forming Assay of Expanded Human Cord Blood CD34+Cells

Following FACS (BD Biosciences, NC) sorting, about 600 cells from the expanded CD34$^{br}$ population and about 2500 cells from the expanded CD34$^{dim}$ population were plated into methylcellulose media containing SCF, IL-3, EPO, and GM-CSF. As a control, about 600 cells from the freshly isolated and enriched CD34+ cell population before culture were placed into the same conditions.

Plating efficiency was found to be:
17.9% (16.45%-31.5%) freshly isolated CD34+ cells (91.1% purity)
9.1% (9.1%-21.3%) CD34$^{br}$ (~95% purity)
6.1% CD34$^{dim}$ (~95% purity)

NOD/SCID Mice Grafts

Seven-week-old male NOD/CB17-Prkdc-SCID/J mice were obtained (Jackson Laboratories, ME) and housed in a micro-isolation cage rack and fed autoclaved food and water. The animal care and use committee of Becton-Dickinson Technologies (BDT) and Duke University Medical Center approved all experiments.

NOD/SCID mice (6-8 week old) received a total dose of 300 cGy from a cesium Cs$^{137}$ source. Within 24 hours following irradiation, the mice were injected intra-bone marrow (iBM) with human UCB CD34$^{br}$ and CD34$^{dim}$ cells that were previously expanded for 7 days. iBM injection was carried out as described previously by Yahata et al. (2003) Blood, 101:2905-13, with slight modifications. In brief, a 29-gauge needle was inserted into the joint surface of the right femur of an anesthetized mouse. Expanded UCB CD34$^+$ cells suspended in 40 µl PBS were injected into the BM cavity. Cell doses delivered are outlined in Table 20.

TABLE 20

Cell Doses for NOD/SCID Mouse Bone Marrow Injection

| CD34$^+$ Bright | | CD34$^+$ Dim | |
|---|---|---|---|
| Cell number | n | Cell number | n |
| PBS + 0.5% BSA | 2 | 1,000,000 | 3 |
| 10,000 | 3 | 456,717 | 1 |
| 100,000 | 3 | | |
| 500,000 | 3 | | |

Transplant Outcome Analysis

Mouse BM, spleen, and peripheral blood (PB) were harvested at 7 weeks post transplant. Analysis for human reconstitution was performed using methods described in the literature. Briefly, cells from the BM, spleen, and PB were analyzed by 2-color flow cytometric analysis. Erythrocytes (RBC) from peripheral blood (PB) (or spleen and BM if necessary) were lysed using 3-4 ml of ACK lysis buffer (incubated at room temperature for 10 min). Cells were washed and resuspended into PBS with 2% FCS at the final volume of 50 µl/tube. A total of 10 tubes were used per mouse for the BM analysis, and an additional 2 tubes each were used for spleen and PB sample analysis. Cells after RBC lysis were incubated with 8 µl of Mouse Fc block to block FcgII/IIIR-mediated nonspecific binding for 5 minutes at 4° C., and were subsequently incubated with the appropriate monoclonal antibodies (about 5 µl each for 30 minutes at 4° C., washed, resuspended in 1% paraformaldehyde in PBS, and analyzed on a FACS (BD Biosciences, NC) flow cytometer. In addition to isotypic controls (IgG$_1$ FITC/IgG$_1$ PE), cells from a non-transplanted mouse were stained with the same antibody combinations. The combination of non-crossreacting PE-anti-human CD45 and FITC-anti-mouse CD45 was used to determine the ratio of human to mouse leukocytes. For further clarification of human subpopulations, various dual antibody panels were be used: CD45 FITC/CD3 PE and CD45 FITC/CD19 PE for lymphoid lineage detection; CD45 FITC/CD14 PE and CD45 FITC/CD33 PE for myeloid lineage detection; CD45 FITC/CD16 PE for NK cell detection; CD45 FITC/CD34 PE for progenitor cell detection; CD45 FITC/CD42a PE for megakaryocyte (MK) lineage detection; and CD45 FITC/glycophorin A PE for erythroid lineage detection. A minimum of 100,000 cells from BM, spleen, and 100,000 cells from PB were analyzed using the FACS (BD Biosciences, NC) for each mouse. Mice were classified as positive for human cell engraftment as defined by SCID repopulating cell (SRC) reconstitution if they showed at least 0.1% human reconstitution (human CD45 versus mouse CD45 expression), including myeloid and lymphoid engraftment (minimum of 10 positive events each per 100,000 BM cells analyzed). FACS analysis was performed using CellQuest™ software.

Results

Cord blood cells expanded in G2 media were engrafted in the bone marrow, spleen, and PB of irradiated NOD/SCID mice. As shown in FIG. 3, a cell dose of 100,000 CD34$^{br}$ cells was sufficient to achieve reliable engraftment in bone marrow. Over 20% engraftment was observed with 500,000 CD34$^{br}$ cells in bone marrow, spleen, and PB; in contrast, 1,000,000 CD34$^{dim}$ cells were not sufficient to achieve engraftment in this model. Expanded CD34$^{br}$ cells were able to reconstitute B-cells (CD19), myeloid progenitor cells (CD33), hematopoietic stem/progenitor cells (CD34), to a very small extent NK-cells (CD16), monocytes (CD14), and platelet precursors (CD42a)(data not shown).

Example 7

Megakaryocyte Expansion in NOD/SCID Mice Via Direct Bone Marrow Injection of Expanded Cell Populations This example illustrates that UCB cells expanded in G2 media engraft in mouse bone marrow and lead to significant megakaryocyte engraftment when injected directly into the bone marrow of irradiated NOD/SCID mice.

Whole cord blood was received from NDRI and processed as described in Example 6. CD34$^+$ cells were cultured in G2 medium for 7 days, then sorted into CD34$^{dim}$ and CD34$^{br}$ cells and then transplanted by direct injection into the bone marrow into sub-lethally irradiated mice as described in Example 6. Freshly isolated CD34$^+$ cells were used as controls. Cell doses that were used, number of transplanted animals, number of engrafted mice and level of engraftment, as defined as the percentage of human CD45$^+$ cells found in the mouse bone marrow 7 weeks following transplant are shown in Table 21.

TABLE 21

Average Engraftment Levels of Freshly Isolated Human CD34$^+$ Cells (Control), CD34$^{br}$ Cells (Expanded in G2 Medium), or CD34$^{dim}$ Cells (Expanded in G2 Medium) in Mouse Bone Marrow 7 Weeks Following Direct Injection

| | Number of Transplanted Animals | | | Number of Engrafted Animals | | | Engraftment Levels | | |
|---|---|---|---|---|---|---|---|---|---|
| Cell Dose | Control | CD34$^{br}$ | CD34$^{dim}$ | Control | CD34$^{br}$ | CD34$^{dim}$ | Control | CD34$^{br}$ | CD34$^{dim}$ |
| 100 | 3 | — | — | 0 | — | — | — | — | — |
| 1,000 | 2 | — | — | 0 | — | — | — | — | — |
| 5,000 | 4 | — | — | 3 | — | — | 0.7 | — | — |
| 10,000 | 6 | 3 | — | 4 | 0 | — | 3.5 | — | — |
| 25,000 | 3 | — | — | 2 | — | — | 4.0 | — | — |
| 50,000 | 5 | 1 | — | 5 | 1 | — | 11.7 | 0.4 | — |
| 75,000 | 1 | — | — | 1 | — | — | 14.2 | — | — |
| 100,000 | 5 | 4 | — | 5 | 3 | — | 15.7 | 1.3 | — |

TABLE 21-continued

Average Engraftment Levels of Freshly Isolated Human CD34+ Cells (Control), CD34$^{br}$ Cells (Expanded in G2 Medium), or CD34$^{dim}$ Cells (Expanded in G2 Medium) in Mouse Bone Marrow 7 Weeks Following Direct Injection

| Cell Dose | Number of Transplanted Animals | | | Number of Engrafted Animals | | | Engraftment Levels | | |
|---|---|---|---|---|---|---|---|---|---|
| | Control | CD34$^{br}$ | CD34$^{dim}$ | Control | CD34$^{br}$ | CD34$^{dim}$ | Control | CD34$^{br}$ | CD34$^{dim}$ |
| 375,000 | — | 1 | — | — | 1 | — | — | 5.6 | — |
| 400,000 | — | 2 | — | — | 2 | — | — | 43.4 | — |
| 500,000 | — | 4 | — | — | 4 | — | — | 15.4 | — |
| 1,000,000 | — | — | 3 | — | — | 0 | — | — | 0 |
| 1,900,000 | — | — | 1 | — | — | 1 | — | — | 15.8 |

According to the data in Table 21, administering 100,000 CD34+, 500,000 CD34$^{br}$, or 1,900,000 CD34$^{dim}$ cells results in about the same engraftment level of approximately 15% human CD45+ cells in the mouse bone marrow.

Surprisingly, administering the CD34$^{br}$ cell population resulted in the highest number of human megakaryocytes, as defined by human CD42a+ cells, contained in the mouse bone marrow (see Table 22).

TABLE 22

Percent Human CD42a+ Cells in Mouse Bone Marrow Following Direct Injection of Human CD34+ Cells

| Transplanted Cells | 100,000 Freshly Isolated CD34+ | 500,000 GD34$^{br}$ | 1,900,000 CD34$^{dim}$ |
|---|---|---|---|
| Percent of cells huCD42a+ | 0.8 | 4.9 | 2.0 |

The percentages of human CD45+ cells present in mouse BM, spleen, and PB following intra-bone marrow injection of freshly isolated CD34+ cells, CD34$^{br}$ cells expanded in G2 medium, or CD34$^{dim}$ cells expanded in G2 medium are shown in Tables 23, 24, and 25, respectively,

TABLE 23

Percent Human CD45+ Cells in Mouse BM, Spleen, and PB Following Intra-Bone Marrow Injection of Freshly Isolated CD34+ Cells

| Cell dose | Mouse # | % huCd45+ cells in mBM | % huCD45+ cells in mSpleen | % huCD45+ cells in mPB |
|---|---|---|---|---|
| 100 | 1-3 | 0 | 0 | 0 |
| 1,000 | 1-2 | 0 | 0 | 0 |
| 5,000 | 1 | 1.05 | 0 | 0 |
| | 2 | 0.97 | 0.02 | 0 |
| | 3 | 0.16 | 0.05 | 0 |
| 10,000 | 1 | 2.13 | 0.1 | 0.1 |
| | 2 | 0.62 | 0 | 0 |
| | 3 | 9.34 | 0 | 0 |
| | 4 | 1.74 | 0 | 0 |
| | 5 | 0 | 0 | 0 |
| 25,000 | 1 | 10.58 | 5.14 | 0.19 |
| | 2 | 1.40 | 0.08 | 0.01 |
| 50,000 | 1 | 1.24 | 0.02 | 0.01 |
| | 2 | 47.01 | 1.93 | 0.19 |
| | 3 | 0.59 | 0 | 0.01 |
| | 4 | 5.79 | 0.44 | 0.01 |
| | 5 | 0 | 0 | 0 |
| 75,000 | 1 | 14.2 | 8.35 | 0.34 |
| 100,000 | 1 | 24.66 | 5.32 | 3.28 |
| | 2 | 18.01 | 0.01 | 1.68 |
| | 3 | 9.02 | 16.06 | 5.25 |
| | 4 | 1.66 | 3.14 | 0.07 |
| | 5 | 25.08 | 12.79 | 1.83 |

TABLE 24

Percent Human CD45+ Cells in Mouse BM, Spleen, and PB Following Intra-Bone Marrow injection of CD34$^{br}$ Cells Expanded in G2 Medium

| Cell dose | Mouse # | % huCd45+ cells in mBM | % huCD45+ cells in mSpleen | % huCD45+ cells in mPB |
|---|---|---|---|---|
| 10,000 | 1-3 | 0 | 0 | 0 |
| 50,000 | 1 | 0.4 | 0.07 | 0.09 |
| 100,000 | 1 | 0.30 | 0.82 | 0 |
| | 2 | 2.75 | 0.63 | 3.72 |
| | 3 | 0.98 | 0.05 | 1.05 |
| | 4 | 0 | 0 | 0 |
| 375,000 | 1 | 5.6 | 0.1 | 0.08 |
| 400,000 | 1 | 61.49 | 18.90 | 0.56 |
| | 2 | 25.36 | 0.29 | 0 |
| 500,000 | 1 | 16.57 | 0.21 | 0.02 |
| | 2 | 16.02 | 0.27 | 0.03 |
| | 3 | 18.61 | 5.36 | 3.48 |
| | 4 | 10.41 | 1.42 | 1.41 |

TABLE 25

Percent Human CD45+ Cells in Mouse BM, Spleen, and PB Following Intra-Bone Marrow Injection of CD34$^{dim}$ Cells Expanded in G2 Medium

| Cell dose | Mouse # | % huCd45+ cells in mBM | % huCD45+ cells in mSpleen | % huCD45+ cells in mPB |
|---|---|---|---|---|
| 1,000,000 | 1-3 | 0 | 0 | 0 |
| 1,900,000 | 1 | 15.8 | 0.36 | 0 |

Example 8

Homing and Megakaryocyte Engraftment after Transplantation of Expanded Cell Populations into NOD/SCID Mice Via Tail Vein Injection This example illustrates that UCB cells expanded in various media of the present invention home and engraft into the mouse bone marrow when injected through the tail vein into the peripheral blood circulation of an irradiated NOD/SCID mouse, which leads to superior megakaryocyte engraftment.

G2 Medium

Whole cord blood was received from NDRI and processed as described in Example 6. $CD34^+$ cells were cultured in the G2 medium for 7 days, then sorted into $CD34^{dim}$ and $CD34^{br}$ cells and then transplanted by tail vein injection into sublethally irradiated mice as described in Example 6. Freshly isolated $CD34^+$ cells were used as controls. Cell doses that were used, number of transplanted animals, number of engrafted mice and level of engraftment, as defined as percentage of human CD45+ cells found in the mouse bone marrow 7 weeks following transplant are shown in Table 25. Data in Table 26 confirms that UCB cells expanded in the G2 medium are able to home to the bone marrow of a recipient mouse when injected into the peripheral blood circulation by tail vein injection.

TABLE 26

Average Engraftment Levels of Freshly Isolated Human $CD34^+$ Cells (Control), $CD34^{br}$ Cells (Expanded in G2 Medium), or $CD34^{dim}$ Cells (Expanded in G2 Medium) in Mouse Bone Marrow 7 Weeks Following Tail Vein Injection

| Cell Dose | Number of Transplanted Animals | | | Number of Engrafted Animals | | | Engraftment Levels | | |
|---|---|---|---|---|---|---|---|---|---|
| | Control | $CD34^{br}$ | $CD34^{dim}$ | Control | $CD34^{br}$ | $CD34^{dim}$ | Control | $CD34^{br}$ | $CD34^{dim}$ |
| 1,000 | 2 | — | — | 0 | — | — | — | — | — |
| 10,000 | 2 | — | — | 0 | — | — | — | — | — |
| 50,000 | 2 | — | — | 2 | — | — | 1.04 | — | — |
| 100,000 | 6 | — | — | 5 | — | — | 11.72 | — | — |
| 250,000 | 1 | — | — | 1 | — | — | 80.79 | — | — |
| 500,000 | 5 | — | — | 5 | — | — | 7.5 | — | — |
| 518,000 | — | 1 | — | — | 1 | — | — | 94.00 | — |
| 850,000 | — | — | 1 | — | — | 0 | — | — | — |
| 1,200,000 | — | — | 1 | — | — | 1 | — | — | 59.19 |
| 1,300,000 | — | 1 | — | — | 1 | — | — | 50.1 | — |
| 1,800,000 | — | — | 1 | — | — | 1 | — | — | 0.2 |

Surprisingly, when further characterizing the engrafted human $CD45^+$ from the mouse bone marrow cells, administration of a similar number of $CD34^{br}$ cells compared to freshly isolated $CD34^+$ cells resulted in the highest number of human megakaryocytes, as defined by human $CD42a^+$ cells contained in the mouse bone marrow (see Table 27).

TABLE 27

Percent Human $CD42a^+$ Cells in Mouse Bone Marrow Following Tail Vein Injection of Human $CD34^+$ Cells

| Transplanted Cells | Percentage of cells $huCD42a^+$ |
|---|---|
| 500,000 freshly isolated $CD34^+$ | 1.2 |
| 518,000 $CD34^{br}$ | 7.8 |
| 1,300,000 $CD34^{br}$ | 8.3 |
| 1,200,000 $CD34^{dim}$ | 10.6 |
| 1,900,000 $CD34^{dim}$ | 0.2 |

The percentages of human $CD45^+$ cells present in mouse BM, spleen, and PB following tail vein injection of freshly isolated $CD34^+$ cells, $CD34^{br}$ cells expanded in G2 medium, and $CD34^{dim}$ cells expanded in G2 medium are shown in Tables 28, 29, and 30, respectively.

TABLE 28

Percent Human $CD45^+$ Cells in Mouse BM, Spleen, and PB Following Tail Vein Injection of Freshly Isolated $CD34^+$ Cells

| Cell dose | Mouse # | % $huCd45^+$ cells in mBM | % $huCD45^+$ cells in mSpleen | % $huCD45^+$ cells in mPB |
|---|---|---|---|---|
| 1,000 | 1-2 | 0 | 0 | 0 |
| 10,000 | 1-2 | 0 | 0 | 0 |
| 50,000 | 1 | 1.32 | 0 | 0 |
| | 2 | 0.76 | 0.2 | 0.04 |
| 100,000 | 1 | 1.19 | 0.21 | 0.02 |
| | 2 | 6.65 | 0.27 | 0.03 |
| | 3 | 18.88 | 1.31 | 0.06 |

TABLE 28-continued

Percent Human CD45+ Cells in Mouse BM, Spleen, and PB Following Tail Vein Injection of Freshly Isolated CD34+ Cells

| Cell dose | Mouse # | % huCd45+ cells in mBM | % huCD45+ cells in mSpleen | % huCD45+ cells in mPB |
|---|---|---|---|---|
| | 4 | 13.85 | 1.48 | 0.03 |
| | 5 | 18.05 | 0.75 | 0.05 |
| | 6 | 0 | 0 | 0 |
| 250,000 | 1 | 80.79 | 18.49 | 0.54 |
| 500,000 | 1 | 7.04 | 4.54 | 0.17 |
| | 2 | 5.52 | 16.09 | 0.74 |
| | 3 | 9.59 | 27.30 | 9.74 |
| | 4 | 11.20 | 9.31 | 3.78 |
| | 5 | 4.24 | 1.30 | 1.58 |

TABLE 29

Percent Human CD45+ Cells in Mouse BM, Spleen, and PB Following Tail Vein Injection of CD34$^{br}$ Cells Expanded in G2 Medium

| Cell dose | Mouse # | % huCd45+ cells in mBM | % huCD45+ cells in mSpleen | % huCD45+ cells in mPB |
|---|---|---|---|---|
| 518,000 | 1 | 94.0 | 31.81 | 10.68 |
| 1,300,000 | 1 | 50.1 | 3.89 | 2.35 |

TABLE 30

Percent Human CD45+ Cells in Mouse BM, Spleen, and PB Following Tail Vein Injection of CD34$^{dim}$ Cells Expanded in G2 Medium

| Cell dose | Mouse # | % huCd45+ cells in mBM | % huCD45+ cells in mSpleen | % huCD45+ cells in mPB |
|---|---|---|---|---|
| 850,000 | 1 | 0 | 0 | 0 |
| 1,200,000 | 1 | 59.19 | 7.57 | 1.71 |
| 1,800,000 | 1 | 5.29 | 0.70 | 1.86 |

The percentages of human CD45+ cells present in mouse BM following tail vein injection of TNCs following a 7 or 9 day expansion in G2 medium are shown in Tables 31 and 32, respectively. The percentages of human CD45+ cells present in mouse spleen following tail vein injections of 2,000,000 TNCs following a 7 day expansion in G2 medium ranged from 4.3% to 35.5%. The percentages of human CD45+ cells present in mouse PB following tail vein injections of 2,000,000 TNCs following a 7 day expansion in G2 medium ranged from 1.1% to 11.3%.

TABLE 31

Percent Human CD45+ Cells in Mouse BM Following Tail Vein Injection of TNCs Expanded in G2 Medium for 7 Days

| Cell dose | Mouse # | % huCd45+ cells in mBM |
|---|---|---|
| 100,000 | 1 | 3.53 |
| 130,000 | 1 | 0.12 |
| 250,000 | 1 | 28.5 |
| | 2 | 25.7 |
| | 3 | 8.5 |
| 360,000 | 1 | 0.50 |

TABLE 31-continued

Percent Human CD45+ Cells in Mouse BM Following Tail Vein Injection of TNCs Expanded in G2 Medium for 7 Days

| Cell dose | Mouse # | % huCd45+ cells in mBM |
|---|---|---|
| 500,000 | 1 | 23.2 |
| | 2 | 67.7 |
| | 3 | 61.7 |
| 1,000,000 | 1 | 55.0 |
| | 2 | 56.0 |
| | 3 | 76.0 |
| 1,500,000 | 1 | 75.3 |
| | 2 | 78.2 |
| 2,000,000 | 1 | 42.5 |
| 2,000,000 | 2 | 29.3 |
| 2,000,000 | 3 | 72.6 |
| 2,000,000 | 4 | 79.2 |

TABLE 32

Percent Human CD45+ Cells in Mouse BM, Spleen, and PB Following Tail Vein Injection of TNCs Expanded in G2 Medium for 9 Days

| Cell dose | Mouse # | Cells injected | % huCd45+ cells in mBM | % huCD45+ cells in mSpleen | % huCD45+ cells in mPB |
|---|---|---|---|---|---|
| $0.5 \times 10^6$ | 1 | TNC | 34.4 | 35.5 | 3.4 |
| $0.5 \times 10^6$ | 2 | TNC | 5.0 | 1.2 | 1.1 |
| $2.0 \times 10^6$ | 1 | TNC | 1.7 | 6.7 | 1.2 |
| $2.0 \times 10^6$ | 2 | TNC | 6.9 | 2.7 | 0.7 |

G8 Medium

The percentages of human CD45+ cells present in mouse BM following tail vein injection of TNCs following a 7 day expansion in G8 medium are shown in Table 33. The percentages of human CD45+ cells present in mouse spleen following tail vein injections of 2,000,000 TNCs following a 7 day expansion in G8 medium ranged from 23.2% to 23.7%. The percentages of human CD45+ cells present in mouse PB following tail vein injections of 2,000,000 TNCs following a 7 day expansion in G8 medium ranged from 2.2% to 10.2%.

TABLE 33

Percent Human CD45+ Cells in Mouse BM Following Tail Vein Injection of TNCs Expanded in G8 Medium for 7 Days

| Cell dose | Mouse # | % huCD45+ cells in mBM |
|---|---|---|
| 350,000 | 1 | 2.71 |
| | 2 | 6.61 |
| 430,000 | 1 | 9.77 |
| $2.0 \times 10^6$ | 1 | 44.6 |
| $2.0 \times 10^6$ | 2 | 64.7 |

F4 Medium

The percentages of human CD45+ cells present in mouse BM, spleen, and PB following tail vein injection of TNCs following a 7 or 9 day expansion in F4 medium are shown in Tables 34 and 35, respectively,

TABLE 34

Percent Human CD45+ Cells in Mouse BM, Spleen, and PB Following Tail Vein Injection of TNCs Expanded in F4 Medium for 7 Days

| Cell dose | Mouse # | % huCd45+ cells in mBM | % huCD45+ cells in mSpleen | % huCD45+ cells in mPB |
|---|---|---|---|---|
| 12,600 | 1 | 0 | 0 | 0 |
| 54,000 | 1 | 0 | 0 | 0 |

TABLE 35

Percent Human CD45+ Cells in Mouse BM, Spleen, and PB Following Tail Vein Injection of TNCs Expanded in F4 Medium for 9 Days

| Cell dose | Mouse | % huCd45+ cells in mBM | % huCD45+ cells in mSpleen | % huCD45+ cells in mPB |
|---|---|---|---|---|
| 0.5 × 10⁶ | 1 | 14.2 | 7.9 | 1.5 |
| 0.5 × 10⁶ | 2 | 0 | 0 | 0 |

Example 9

Secondary Mouse Engraftment Studies

For these studies, methods were as described above in Example 6 for primary mouse engraftment. Mice transplanted with expanded $CD34^{br}$ or $CD34^{dim}$ cells were sacrificed 7 weeks post-transplant. Mouse BM from both femur and tibia was flushed out using a 25 gauge needle. The BM cells were washed and resuspended with PBS plus 2% FCS. The cells were counted with trypan blue and injected through the tail vein into a second group of sub-lethally irradiated NOD/SCID mice. The second group of mice were sacrificed 7 weeks post-transplant. The mouse bone marrow was analyzed as described above in Example 6.

Results

Both the $CD34^{br}$ and $CD34^{dim}$ cells expanded in G2 medium were able to give rise to long term engraftment of human hematopoietic cells and reconstitute the second irradiated NOD/SCID mouse bone marrow. Table 36 shows the percentage of human CD45+ cells in mouse BM following primary and secondary transplant of $CD34^{br}$ or $CD34^{dim}$ cells expanded in G2 medium.

Example 10

Culture and Expansion of Adherent, Stromal-Like Cells Derived from UCB

This example illustrates that stromal-like cells can be enriched by adherence to plastic tissue culture surfaces from UCB when using G2 medium.

Whole blood was received from NDRI and the white blood cell fraction was isolated by eliminating red blood cells by first using hetastarch, followed by lysis buffer treatment as described in Example 2. The total nucleated white cell fraction was seeded at a seeding density of 1,000,000 TNCs/well/6 ml of G2 medium into 6-well plates, or at a seeding density of 5,000,000 TNCs/T-25 flask/15 ml of G2 medium, and incubated for 16 days. An adherent cell layer formed within about 24 hrs of initiating the culture. Morphology of the adherent cells is indicative of stromal-like, epithelial cells.

Example 11

Gene Expression Profile of Expanded $CD34^{br}$ Cells

RNA Purification

RNA was purified from CD34+ cells that were separated from 2-day refrigerated UCB on day 0 and after cell culture on day 1 and day 7. RNA purification was performed using the Qiagen RNeasy method (Qiagen catalog number 74104). Approximately 2×10⁶ CD34+ cells were collected by centrifugation at 400×g for 10 minutes at room temperature and the medium was removed.

Mercaptoethanol was added to the RLT lysis buffer just prior to use, (v/v) 10 µl per ml. Cells were lysed by addition of 350 µl of RLT chaotrope-lysis buffer and pipet mixed several times then vortex mixed. The lysate was transferred to a QIAshredder spin column in a 2 ml collection tube and centrifuged for 2 minutes at maximum speed (Q16,000×g) to homogenize. One volume of 70% ethanol was added to the lysate and pipet mixed. The lysate was transferred to an RNeasy spin column in a 2 ml collection tube and centrifuged for 15 seconds at 10,000×g to bind RNA to the column matix.

TABLE 36

Human CD45+ cells in Mouse BM Following Primary and Secondary Transplant of Expanded $CD34^{br}$ or $CD34^{dim}$ cells

| | | Primary mice transplant (week 8) | | Secondary transplant (week 6) | | |
|---|---|---|---|---|---|---|
| Route | Cell dose | culture in G02 Media | % huCD45 in mouse BM | Cell dose (million) | Route | % huCD45 in mouse BM |
| iBM (N = 1) | 400,000 | CD34br expanded | 61.49 | 24.47 | IV | 0.73 |
| | 400,000 | CD34br expanded | 25.36 | 29.15 | IV | 0.36 |
| | 1,900,000 | CD34dim expanded | 15.83 | 29.25 | IV | 0.14 |

The flow-thru was discarded and the column matix washed by addition of 350 µl of RW1 wash buffer and centrifugation as above.

An on-column DNase treatment was performed using the Qiagen Rnase-free DNase set cat #79254, described in brief below. Eighty µl of reconstituted/diluted DNAse (10 µl reconstituted DNAse+70 µl RDD buffer) was added to the center of the spin column membrane and incubated at room temperature for 15 minutes. The spin column was then washed a second time by addition of 350 µl RW1 and then centrifuged for 1 minute at 10,000 rpm.

The spin column was then placed in a new collection tube and washed by addition of 500 µl RPE buffer and centrifugation for 1 minute at 10,000 rpm. The flow-thru was discarded and another 500 µl RPE buffer was applied to the spin column followed by centrifugation for 3 min at 13,200 rpm. The spin column was transferred to a new 1.7 ml capped microtube. To make sure that no ethanol remains on the spin column the sample was centrifuged again for 1 minute at maximum speed. The column was transferred to a clean microtube and the RNA was eluted by 2 additions of 30 µl RNAse free water to the center membrane and centrifuging for 1 minute at 10,000×g.

Microarrays

RNA samples were compared for gene expression (transcript) profile differences using Agilent human oligo IA 22K arrays. The microarray hybridizations/scans were contracted to Paradigm Genetics. They performed data extraction and normalizations using the Agilent scanner and Rosetta Resolver. BDT-bioinformatics also normalized the extracted data with algorithms developed at BDT.

Both sets of sets of normalized data were then evaluated for up and down regulated transcripts in day 7 CD34$^{br}$ versus CD34$^{dim}$ cell populations and in day 0 versus day 1 cultured CD34$^+$ cells. Groupings of differentially expressed genes were studied for patterns related to gene function discerned from the literature. Interesting sub-groups were established based on related gene functions and these relationships suggested some specific biological interpretations that can be or were further tested. For example, out of over 16,000 measurable transcripts from the Rosetta array normalizations, the day 7 CD34$^{br}$ cell population had only 19 transcripts that were more that 2.5 fold elevated compared to the CD34$^{dim}$ population. Several of these transcripts, DLK1, CSRP2, and PROML1 (CD 133) have functions or associations described in the literature related to multi-potent stem/progenitor cells characterized by proliferation and non-differentiation. Based on the BDT normalization, only 15 transcripts were elevated more than 2 fold and were determined to be statistically significant changes. These again included both DLK1 and CSRP2. In addition, transcript STMN3 also belonging to this class was included. The stem cell transcript PROML1 (CD 133) was elevated 2.0 fold but for the BDT normalizations was not determined to be a statistically significant change based on the variations in measurements with these samples.

A larger number of transcripts (81 for the BDT normalized data) were down regulated in the CD34$^{br}$ population compared to the dim population. Many of these transcripts that were less expressed in the bright population have functions related or associated with further hematopoietic cell differentiation. These results characterize the CD34$^{br}$ cell population as an earlier stage, more pluripotent stem cell compared to the more differentiated dim cell population. However, some other known stem cell-associated transcripts such as CD34, CD90 (Thy1), SZF1, C17, IK, PODLX3, FLT1, FLT3, FLT4, CD33, KITLG were at similar levels in the bright and dim population.

Paradigm Genetics Rosetta array measured 16,388 total transcripts. In CD34$^{br}$ cells, 19 genes were up greater than 2.5 fold and P<0.01; whereas 95 genes were down at least 2.5 fold and P<0.01. In the BD Technologies array, 15 genes were up greater than 2 fold. For example, DLK1, which regulates hematopoiesis and inhibits differentiation, was up 3.0 fold. STMN3, which has a role in cell proliferation, was up 2.0 fold. CSRP2, which is a transcription factor that promotes proliferation and differentiation was up 2.6 fold. In the BD Technologies array, 81 genes were down at least 2 fold. The genes related to differentiation and inflammation were down regulated after culture. Over time, transcripts related to cell homing were differentially expressed. CD34$^{br}$ cells showed decreased levels of delta-like protein-1, cysteine and glycine-rich protein 2, FADD, S100A9, and ITB2 mRNA transcripts.

Example 12

Neovascularization of a 3-D Scaffold Containing CD34$^{br}$ Cells

Results

When alginate scaffolds were seeded with enriched CD34$^+$ umbilical cord blood cells (80-90% purity), and cultured for 7 days in Stemline™ nutritive medium admixed with G2 medium (with and without VEGF), and then implanted subcutaneously in SCID/NOD mice, neovascularization was observed versus scaffolds containing CD34$^-$ cells. The presence of VEGF greatly enhanced neovascularization within the scaffold containing CD34$^+$ cells.

Example 13

Neovascularization by CD34$^{br}$ Cells in a Pancreatic Repair Model

Whole cord blood was received from NDRI and processed as described in Example 6. CD34$^+$ cells were cultured in G2 medium for 7 days, then sorted into CD34$^{dim}$ and CD34$^{br}$ cells and then transplanted into a murine regenerating pancreas model.

Results

Four weeks post transplantation in a murine regenerating pancreas model, CD34$^{br}$ cells integrated into regenerating pancreas tissue forming long tube-like structures, potentially being vasculature; whereas CD34$^{dim}$ cells formed only dense, unintegrated nodules at the border of the actively remodeling pancreatic tissue.

Example 14

Quantitation of CD34 Expression Using QuantiBRITE™ PE Beads

The present example quantifies CD34 expression on expanded CD34$^{br}$ cells from G2 medium using QuantiBRITE™ PE Beads (Becton-Dickinson, USA) as described elsewhere herein.

CD34$^+$ cells were isolated and cultured for 7 days as described in Example 1 using G2 medium. The expanded cells were suspended at 1×10⁶ cells/100 µl in PBS with 1% BSA (bovine serum albumin) in TruCOUNT™ (Becton-Dickinson) tubes and the cells were stained with 20 µl of CD34-PE 1:1 (Becton Dickinson Immunocytochemistry Systems, San Jose, Calif.) for 15 minutes at room temperature in the dark. After incubation, 1 ml of freshly made 1× PharMLyse™ (BD Pharmingen) and 20 µl of ViaProbe (BD Pharmingen) were added to the cell suspension, followed by incubation for 10 minutes at room temperature in the dark.

During incubation, the QuantiBRITE™ PE Beads were analyzed by QuantiQuest software to establish a standard curve for antibody bound per cell (ABC) value.

The samples were collected within 30 minutes after incubation by FACS (BD Biosciences, NC), and the data were analyzed by ISHAGE method to include the histogram median/peak channel. The value of the median/peak channel for CD34-PE was compared to the standard curve to obtain ABC values for CD34 expression.

Results

The amount of CD34 antigen expression was quantitatively measured on expanded CD34⁺ cells. Table 37 shows the ratio of ABC values from CD34$^{br}$ and total CD34⁺ cells as measured using QuantiBRITE™ PE Beads. Ten experimental runs were conducted and produced ABC ratio values ranging from 1.55 to 3.03.

TABLE 37

Quantitation of CD34 Expression on Expanded CD34$^{br}$ Cells Using QuantiBRITE ™ PE Beads

| Experiment # | CD34$^{br}$ ABC | Total CD34⁺ ABC | ABC Ratio (CD34$^{br}$/CD34⁺ total) |
|---|---|---|---|
| 1 | 120012 | 65837 | 1.82 |
| 2 | 80723 | 41455 | 1.95 |
| 3 | 74144 | 36218 | 2.05 |
| 4 | 81150 | 37628 | 2.16 |
| 5 | 71579 | 32860 | 2.18 |
| 6 | 71504 | 29764 | 2.40 |
| 7 | 66220 | 21867 | 3.03 |
| 8 | 70787 | 37323 | 1.90 |
| 9 | 58237 | 31015 | 1.88 |
| 10 | 62167 | 40045 | 1.55 |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A cell culture medium for expanding a population of stem and progenitor cells comprising basic fibroblast growth factor (bFGF; 1-5 ng/ml), erythropoietin (EPO; 1-6 units/ml), Flt-3/Flk-2 ligand (2-10 ng/ml), interleukin-11 (IL-11; 0.05-0.2 ng/ml), interleukin-6 (IL-6; 0.1-0.5 ng/ml), platelet-derived endothelial cell growth factor (PD-ECGF; 1-4 ng/ml), thrombospondin (5-20 ng/ml), and thrombopoietin (TPO; 0.5-2 ng/ml).

2. The cell culture medium of claim 1, wherein the cell culture medium comprises bFGF (2.5 ng/ml), EPO (3 units/ml), Flt-3/Flk-2 ligand (5 ng/ml), IL-11 (0.1 ng/ml), IL-6 (0.2 ng/ml), PD-ECGF (2 ng/ml), thrombospondin (10 ng/ml), and TPO (1 ng/ml).

3. A method of producing an expanded population of hematopoietic stem and progenitor cells expressing the CD34 cell surface marker, said method comprising culturing a population of CD34⁺ stem and progenitor cells in a cell culture medium comprising bFGF (1-5 ng/ml), EPO (1-6 units/ml), Flt-3/Flk-2 ligand (2-10 ng/ml), IL-11 (0.05-0.2 ng/ml), IL-6 (0.1-0.5 ng/ml), PD-ECGF (1-4 ng/ml), thrombospondin (5-20 ng/ml), and TPO (0.5-2 ng/ml), thereby producing an expanded population of hematopoietic stem and progenitor cells expressing the CD34 cell surface marker.

4. The method of claim 3, wherein the cell culture medium comprises bFGF (2.5 ng/ml), EPO (3 units/ml), Flt-3/Flk-2 ligand (5 ng/ml), IL-11 (0.1 ng/ml), IL-6 (0.2 ng/ml), PD-ECGF (2 ng/ml), thrombospondin (10 ng/ml), and TPO (1 ng/ml).

* * * * *